(12) United States Patent
Hedberg et al.

(10) Patent No.: US 8,527,051 B1
(45) Date of Patent: Sep. 3, 2013

(54) DETECTION AND REDUCTION OF PHRENIC NERVE STIMULATION

(75) Inventors: Sven-Erik Hedberg, Kungsangen (SE); Tomas Svensson, Stockholm (SE); Kjell Noren, Solna (SE); Stuart Rosenberg, Castaic, CA (US); Kyungmoo Ryu, Palmdale, CA (US); Edward Karst, South Pasadena, CA (US)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 13/545,776

(22) Filed: Jul. 10, 2012

(51) Int. Cl.
*A61N 1/37* (2006.01)

(52) U.S. Cl.
USPC .............................................. 607/18; 607/11

(58) Field of Classification Search
USPC .......................................................... 607/18
See application file for complete search history.

(56) References Cited

U.S. PATENT DOCUMENTS

| | | | |
|---|---|---|---|
| 6,512,949 B1 | 1/2003 | Combs et al. | |
| 6,772,008 B2 | 8/2004 | Zhu et al. | |
| 7,228,173 B2 | 6/2007 | Cazares | |
| 7,392,086 B2 | 6/2008 | Sathaye | |
| 7,426,412 B1 | 9/2008 | Schecter | |
| 7,672,729 B2 | 3/2010 | Koh et al. | |
| 2003/0065365 A1 | 4/2003 | Zhu et al. | |
| 2005/0060002 A1 | 3/2005 | Zhu et al. | |
| 2010/0305638 A1 | 12/2010 | McCabe et al. | |
| 2010/0305647 A1* | 12/2010 | McCabe et al. | 607/18 |

* cited by examiner

*Primary Examiner* — Michael Kahelin

(57) ABSTRACT

The present invention provides implantable medical devices for detecting phrenic nerve stimulation. A pacing module is configured to deliver pacing pulses having a predetermined pulse amplitude and/or width within the refractory period of the left ventricle. The pacing pulses are repeatedly delivered during a number of cardiac cycles, and the pacing pulses are delivered at different delays relative to an onset of the refractory period of the left ventricle in different cardiac cycles. An impedance measurement module is configured to measure impedance signals in time windows synchronized with the delivery of pacing pulses in the refractory period of the left ventricle. A phrenic nerve stimulation, PNS, detection module is configured to gather at least one impedance signal from each time window, create aggregated impedance signals using the impedance signals from the different time windows, and analyze the aggregated impedance signals to detect PNS.

29 Claims, 12 Drawing Sheets

$A_1 + \ldots + A_n >$ predetermined limit $A'_1 + \ldots + A'_n <$ predetermined limit

DETECTION AND REDUCTION OF PHRENIC NERVE STIMULATION

CROSS REFERENCE TO RELATED APPLICATIONS

This application is related to U.S. patent application Ser. No. 13/545,794, filed Jul. 10, 2012, titled "Detection and Reduction of Phrenic Nerve Stimulation".

FIELD OF THE INVENTION

The present invention relates generally to methods and implantable medical devices and more particularly to methods and devices for detecting and reducing undesired phrenic nerve stimulation.

BACKGROUND OF THE INVENTION

Implantable cardiac stimulation devices are well known in the art. Such devices may include, for example, implantable cardiac pacemakers and defibrillators either alone or combined in a common enclosure. The devices are generally implanted in a pectoral region of the chest beneath the skin of a patient within what is known as a subcutaneous pocket. The implantable devices generally function in association with one or more electrode(-s) carrying leads which are implanted within the heart. The electrodes are positioned within the heart for making electrical contact with the muscle tissue of respective heart chamber. Conductors within the leads connect the electrodes to the device to enable the device to deliver the desired electrical therapy. Hence, cardiac rhythm management devices are implantable devices that provide electrical stimulation to selected chambers of the heart in order to treat disorders of cardiac rhythm. Common conditions for which pacemakers are used are the treatment of bradycardia, where the ventricular rate is too low, and heart failure.

A programmable electronic controller of the device causes pacing pulses to be output in response to lapsed timing intervals and sensed electrical activity (i.e. intrinsic heart beats not as a result of a pacing pulse). Pacemakers sense intrinsic cardiac electrical activity by means of electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or ventricular pace) with energy above a certain pacing threshold is delivered to the chamber via the same electrode or via other electrodes than used for sensing the chamber.

Bi-ventricular pacing provides therapy options for a patient suffering from heart failure. However, new challenges have been presented by placement of the left-ventricular lead via the coronary sinus in bi-ventricular pacing systems. Due to the proximity of the coronary veins to the phrenic nerve, left ventricular pacing may result in undesirable phrenic nerve stimulation. The left phrenic nerve, which provides innervation for the diaphragm, arises from the cervical spine and descends to the diaphragm through the mediastinum where the heart is situated. As it passes the heart, the phrenic nerve courses along the pericardium, superficial to the left atrium and left ventricle. Because of its proximity to the electrodes used for pacing, the nerve can be stimulated by a pacing pulse. The resulting involuntary contraction of the diaphragm can be annoying to the patient and may also interfere with breathing.

Accordingly, there exist various methods and devices for detecting and reducing phrenic nerve stimulation of cardiac pacing systems within the art.

In U.S. Pat. No. 7,392,086 to Sathaye methods involving delivery of pacing pulses, sense of transthoracic impedance signals following the pacing pulses and analysis of deviations in the transthoracic impedance signals are disclosed. More specifically, a transthoracic impedance signal is analysed in a time window following a left-ventricular pace pulse, e.g. 500 milliseconds long time windows starting at the delivery of a left-ventricular pulse, by comparison with a transthoracic impedance signal resulting from an additional pulse delivered during a cardiac refractory period of the left ventricle to find deviations indicating phrenic nerve stimulation. A threshold test for the available particular pacing vectors may be performed to find and select the best vector in terms of desirable energy levels and reduced phrenic nerve stimulation.

In U.S. Patent Application No. 2010/0305638 to McCabe et al, methods for phrenic nerve activation detection and phrenic nerve activation avoidance are disclosed. According to these methods, impedance is used to identify portions or phases of respiration of interest for detection of phrenic nerve stimulation. Accelerometer signals or other vibration signals are used to detect diaphragmatic response due to phrenic nerve stimulation. The detection is performed within a detection window initiated based on delivery of a left ventricular pulse during a respiration phase of interest.

In U.S. Patent Applications Nos. 2003/0065365 and 2005/0060002 both to Zhu et al., a cardiac rhythm management device in which an accelerometer is used to detect diaphragmatic or other skeletal muscle contraction associated with output of a pacing pulse are disclosed. Upon detection of diaphragmatic contraction, the device may adjust pacing pulse energy and/or pacing configuration.

However, there is still a need within the art for improved methods and devices for detecting phrenic nerve stimulation and for reducing the presence of phrenic nerve stimulation.

SUMMARY OF THE INVENTION

An object of the present invention is to provide improved methods and devices for detecting undesired phrenic nerve stimulation.

A further object of the present invention is to provide improved methods and devices for reducing undesired phrenic nerve stimulation.

Another object of the present invention is to provide improved methods and devices for increasing the accuracy in the phrenic nerve stimulation detection.

These and other objects of the present invention are achieved by means of an implantable medical device and a method having the features defined in the independent claims. Embodiments of the invention are characterized by the dependent claims.

According to an aspect of the present invention, there is provided an implantable medical device connectable to a plurality of electrodes electrically coupled to a heart of a patient in at least one electrode configuration. The device comprises a pacing module configured to deliver pacing pulses to the heart using the at least one electrode configuration and a control module configured to instruct the pacing module to deliver pacing pulses having a predetermined pulse amplitude and/or width within the refractory period of the left ventricle, wherein the pacing pulses are repeatedly delivered during a number of cardiac cycles and wherein the pacing pulses are delivered at different delays relative to an onset of the refractory period of the left ventricle in different cardiac cycles. An impedance measurement module is configured to measure impedance signals in time windows synchronized with the delivery of pacing pulses in the refractory period of the left ventricle using at least one electrode configuration. Further, a phrenic nerve stimulation, PNS, detection module is configured to gather at least one impedance signal from each time window, create aggregated impedance signals using the impedance signals from the different time windows and analyze the aggregated impedance signals to detect PNS.

According to another aspect of the present invention, there is provided a method for detecting PNS. The method comprises delivering pacing pulses having a predetermined pulse amplitude and/or width within the refractory period of the left ventricle using at least one electrode configuration, wherein the pacing pulses are repeatedly delivered during a number of cardiac cycles and wherein the pacing pulses are delivered at different delays relative to an onset of the refractory period of the left ventricle in different cardiac cycles and measuring impedance signals in time windows synchronized with the delivery of pacing pulses in the refractory period of the left ventricle using at least one electrode configuration. Further, at least one impedance signal from each time window is gathered, aggregated impedance signals using the gathered impedance signals from the different time windows are created and the aggregated impedance signals are analyzed to detect PNS.

The present invention is based on the insight that the excursions or deviations of the impedance signal caused by the phrenic nerve stimulation, PNS, move in time in synchronism with the stimulation pulse delivered to the left ventricle and hence can be used for detection of PNS with a high degree of accuracy. Stimulation pulses are delivered in a small time window inside the refractory period of the left ventricle to ensure that stimulation of the ventricles are avoided at the same time as it can be detected whether the delivery of the stimulation pulse results in a PNS. The time windows are broad enough to capture the PNS caused excursions or deviations, and are synchronized with the stimulation pulse in the left ventricle. The stimulation pulses are delivered with different timings relative to the onset of the refractory period of the left ventricle and since the time windows are synchronized with the stimulation pulses, the time windows will move from beat to beat relative the refractory period of the left ventricle. The impedance signals are recorded within the time windows and are collected beat by beat. The impedance signal measured during a PNS will demonstrate significant morphological excursions or deviations caused by the PNS compared to non-PNS impedance signals. Hence, if a PNS occur there exist PNS footprints in the impedance signals that can be used for the PNS detection. By creating an aggregated impedance signal based on measurements during several time windows, each comprising a pace stimulated PNS, the PNS footprint can be enhanced due to the synchrony of the pace delivery and the PNS excursion or deviation in the impedance signal. Thus, the PNS content of the impedance signals can be enhanced by synchronized summation of the signals of the time windows and the PNS content is expected to sum up while uncorrelated signal content within the time windows will be reduced.

According to embodiments of the present invention, PNS templates are created reflecting an impedance signal without PNS content or reflecting an impedance signal including a PNS event. In the first case, detection of PNS can be made by comparing a recorded impedance signal (e.g. an aggregated signal based on recordings from several time windows) with a suitable template and PNS is detected if the recorded impedance signal deviates from the template signal by at least a predetermined limit value. In the second case, i.e. a template with verified PNS content, detection of PNS can be made by comparing a recorded impedance signal (e.g. an aggregated signal based on recordings from several time windows) with the suitable template and PNS is detected if a deviation between the recorded impedance signal and the template signal is below a predetermined limit value. The comparison can be made on a window-by-window basis, i.e. the impedance signal in each window is subtracted from the template signal and the difference signal can then be processed to determine whether a deviation is above a limit (in case the template is free from PNS content) or below a limit (in case the template includes verified PNS content).

According to embodiments of the present invention, it is verified by the patient and/or by the physician whether a PNS occurred or not during the template creation. For example, if the template creation takes place at a clinic, the physician may place a hand on the chest of the patient during the template creation procedure to judge whether a PNS has occurred or not by sensing if spasms or twitches occur in the diaphragm. The physician may thereafter notify the medical device that a PNS has occurred or not using an extracorporeal device such as a programmer capable of communicating with the implanted device. The PNS detection module may hence be configured to receive a verification whether a PNS has occurred or not during the gathering of impedance signals, the verification being received from an extracorporeal unit via a communication module of the implantable medical device and determine whether a created impedance signal template is a template with PNS content or without PNS content depending on the received verification. In an alternative embodiment, the patient may provide the feedback to the medical device, for example if the template creation procedure is performed at home, by sensing if spasms or twitches occur in the diaphragm. The implanted device may be notified via an external unit placed at the home of the patient capable of communicating with the implanted device. This can be executed with or without supervision of a physician from a remote clinic.

According to embodiments of the present invention, the device automatically verifies whether a PNS has occurred or not during the template creation procedure. The PNS detection module is configured to, during a template creation procedure, analyze the gathered impedance signals to determine whether a PNS has occurred or not. This includes, for each time window, calculating the frequency content of the impedance waveform, determining a frequency content related to respiration, and detecting that a PNS has occurred if the frequency content related to respiration is above a predetermined frequency content limit and determining whether a created impedance signal template is a template with PNS content or without PNS content depending on whether a PNS was detected or not. If impedance signals are obtained from a number of different impedance measurement vectors, these can be analyzed in the frequency plane with regard to the respiration content in relation to the heart frequency components and/or remaining frequency content. The impedance vector disclosing the largest relative respiration component is then used for PNS detection. During the template creation procedure, a PNS can be verified if the respiration content of an impedance signal within a time window during a refractory period of the left ventricle is above a predetermined limit. The same impedance vector is accordingly used as a reference to verify whether a PNS has occurred or for the template creation for all impedance vectors.

According to embodiments of the present invention, different templates are created for different postures and/or activity levels and/or stimulation vectors, i.e. electrode configurations used for delivery of pacing pulses. This will improve the accuracy of the PNS detection since the impedance is sensitive to the posture of the patient. For example, the heart will shift position in the chest depending on whether the patient lies in supine or stands or sits, which will result in slightly different electrode configurations with respect to the heart and other organs. This will in turn affect the impedance signal morphology. Further, the location of the leads with respect to the phrenic nerve will also change with different posture, and thus the phrenic nerve stimulation limit may also change. Thereby, by creating templates for different postures and/or different activity levels and/or stimulation vectors, the accuracy of the PNS detection and PNS reduction can be enhanced.

According to embodiments of the present invention, tests or procedures for detecting PNS are regularly performed. The PNS test or PNS detection procedure is performed at regular intervals and/or at detection of a specific posture and/or a specific activity level and/or at occurrence of a predetermined hemodynamic event. The PNS test may include to:

deliver a pacing pulse having a predetermined amplitude/width within a refractory period of the left ventricle, wherein pacing pulses are repeatedly delivered during a number of cardiac cycles;

measure impedance signals in time windows synchronized with the delivery of pacing pulses in the refractory period of the left ventricle using at least one electrode configuration;

gather at least one measured impedance signal from each time window, and analyze the gathered impedance signals to detect morphological events and/or deviations indicating PNS by comparing the gathered impedance signals with an impedance signal template.

In embodiments of the present invention, the hemodynamic events include, for example, an oxygen saturation of the blood being below a predetermined limit, a contractility being below a predetermined limit, blood pressure (e.g. left ventricle pressure changes) being below or above predetermined limits or a heart sound (e.g. first heart sound, S1, and/or second heart sound, S2) indicating a change of the functioning of the heart. To this end, optical sensors can be used for sensing the oxygen saturation, accelerometers can be used to measure contractility, pressure sensors can be used to sense pressure and heart sound microphones can be used to measure the heart sounds. Changes or defects in the electrode system, such as electrode displacements, interruptions in leads, or isolation defects may lead to changes in the hemodynamics. These changes may affect the heart function, limit values and impedance morphology.

According to embodiments of the present invention, a PNS threshold gap between a PNS threshold and a pacing therapy threshold is determined, wherein, at a PNS threshold gap being below a predetermined value, an adaptation of pacing settings of the implantable medical device is performed. The adaptation of pacing settings may include changing electrode configuration for delivery of pacing pulses and/or adapting pacing energy and/or adapting pulse characteristics.

According to embodiments of the present invention, the PNS test includes measuring impedance signals in time windows synchronized with the delivery of a pacing pulse in the refractory period of the left ventricle using more than one electrode configuration in a time window or alternately using different electrode configurations for different time windows. Furthermore, at least one measured impedance signal is gathered from each time window and for each electrode configuration and the gathered impedance signals for each electrode configuration are compared with a corresponding impedance signal template for each electrode configuration and a PNS factor is applied for each electrode configuration.

The absolute differences between each sample of the templates with PNS and the template without PNS are summed for each time window. The time window sums are then averaged over the applicable time windows. This should be performed for each impedance configuration. Each average sum ($A_i$, i=index for impedance configuration) will then be multiplied with a PNS factor being separate for each impedance configuration. The value of each PNS factor is controlled by the following rule:

$$A1*PNSfactor1 = A2*PNSfactor2 = \ldots = Ak*PNSfactork$$

The steps above should be carried out for each body posture and activity. When the impedance signals from each impedance configuration shall be combined as input to the PNS detection analysis, each impedance signal shall be multiplied with the PNS factor belonging to respective impedance configuration. If the PNS detection is carried out using frequency spectra the same procedures as above can be carried out using the frequency components in the selected frequency range instead of the impedance signals. The calculated differences mentioned above are in this case obtained by subtraction of each spectral component of the spectrum with and without PNS. According to embodiments of the present invention, combinations of impedance measurement vectors are used for detecting PNS. At regular intervals and/or at detection of a specific posture and/or a specific activity level and/or at occurrence of a predetermined hemodynamic event the PNS test is performed. The pacing module repeatedly delivers pacing pulses within a refractory period of the left ventricle of the heart during a number of cardiac cycles, which pacing pulses have a predetermined amplitude/width. The impedance measurement module measures impedance signals in time windows synchronized with the delivery of a pacing pulse in the refractory period of the left ventricle using more than one electrode configuration in a time window or alternately using different electrode configurations for different time windows. Further, the PNS detection module gathers at least one measured impedance signal from each time window and for each electrode configuration and analyzes the gathered impedance signals to detect morphological events and/or deviations indicating PNS by comparing the gathered impedance signals for each electrode configuration with a corresponding impedance signal template for each electrode configuration and applying a PNS factor for each electrode configuration.

In embodiments of the present invention, a difference waveform between a measured impedance waveform and each corresponding template for each electrode configuration is calculated and a difference value for each electrode configuration is determined. Each difference value is multiplied with the corresponding PNS factor to determine a resulting value for each electrode configuration, the resulting values for all electrode configurations are added and is determined that PNS has occurred if the added resulting value is higher than a predetermined PNS threshold.

According to embodiments of the present invention, a PNS factor is calculated for each electrode configuration reflecting a difference between an impedance signal template with PNS content and an impedance signal template without PNS content for that specific electrode configuration. Alternatively, the PNS factor for each electrode configuration reflect a difference between frequency content in an impedance waveform with PNS content and frequency content in an impedance waveform without PNS content.

According to embodiments of the present invention, a template (e.g. for a particular posture and/or activity level) can be created based on intrinsic data, i.e. impedance signals obtained during intrinsic activity (without any pacing stimulation). Following an intrinsic left ventricular activation, the impedance can be recorded in time windows starting in the refractory period of the left ventricle. A template can be created for each time window (based on recordings from several heart beats) for that particular posture and/or activity level. One template may be created for that particular posture and/or activity level and time window based on aggregated impedance recordings from a number of cardiac cycles. A template (or templates) created according to this procedure will reflect impedance signals without PNS content.

In embodiments of the present invention, a template (e.g. for a particular posture and/or activity level) can be created based on ventricular stimulation, i.e. impedance signals resulting from pacing stimulation. Following a left ventricular activation, the impedance can be recorded in time windows starting in the refractory period of the left ventricle. A template can be created for each time window (based on recordings from several heart beats) for that particular posture and/or activity level. One template may be created for that particular posture and/or activity level and time window based on aggregated impedance recordings from the number of cardiac cycles. The stimulation in the left ventricle should not result in a PNS (in case templates without PNS content is desired), which may be the case if the margin between the pacing energy and the PNS threshold is small. For example, the PNS threshold can be determined and the pacing energy can be reduced below this threshold to secure that no PNS occurs.

According to embodiments of the present invention, a template (e.g. for a particular posture and/or activity level) can be created based on impedance signals with PNS content resulting from a delivered PNS test pulse within the refractory period of the left ventricle. Preferably, the template is created from impedance data collected over a number of heart beats, i.e. from a number of time windows. One PNS test pulse is delivered during the refractory period of the left ventricle of each heart beat. The impedance signals can be averaged over the heart beats in order to remove disturbing signal content such as respiration variations. Preferably, the delivered pacing energy is above a verified PNS threshold so as to secure that the pacing pulse results in PNS.

According to embodiments of the present invention, the template creation is more frequent during a period of time close to an implantation of the cardiac device. For example, templates can be created once a day during the period of time close to the implantation and then successively be created less frequently during the course of time. The templates are preferably created for different postures and different activity levels, and possibly also for different pacing and impedance vectors. However, a stable electrode system, i.e. a system that has been implanted during a relatively long period of time, may require a more frequent update of the templates in certain situations. For example, the lead positions relative to the phrenic nerve may change over time, which may increase the risk for PNS significantly. The electrode system should therefore be monitored. One such monitoring method is to measure lead impedance and a change above a predetermined threshold may trigger a template creation procedure. Another monitoring method is to measure QRS amplitudes and a change above a predetermined threshold may trigger a template creation procedure. A further method is to monitor changes in the impedance vector's morphologies and a change above a predetermined threshold may trigger a template creation procedure. Yet another way is to monitor the pacing threshold (of the heart) and an increase above a predetermined threshold may trigger a template creation procedure. These different methods for monitoring the electrodes can also be combined.

According to embodiments of the present invention, the control module is configured to instruct the pacing module to deliver the pacing pulses at the different delays relative to the onset of the refractory period of the left ventricle in different cardiac cycles, wherein the onset of the refractory period of the left ventricle is determined to be a delivery of a stimulation pulse resulting in a ventricle contraction or a spontaneous ventricle contraction.

According to embodiments of the present invention, the control module is configured to instruct the pacing module to deliver the pacing pulses via at least a first electrode configuration and wherein the impedance measurement module is configured to measure at least one impedance signal using at least a second electrode configuration.

According to embodiments of the present invention, the control module is configured to perform a template creation procedure at predetermined time intervals or at receipt of an instruction.

According to embodiments of the present invention, the control module is configured to monitor changes in lead system criteria and, at detection of a change in at least one lead system criteria exceeding a predetermined threshold, to perform a template creation procedure and/or instruct the pacing module to change electrode configuration for delivery of pacing pulses and/or to issue an alert. The lead system criteria indicates changes in the function of the lead system due to, for example, changes in the location of electrodes, changes in the functioning of electrodes, which, in turn affect the potential phrenic nerve stimulation, e.g. phrenic nerve stimulation threshold, or the gathering of impedance signals. Examples of such lead system criteria include, but are not limited to, lead impedance (electrode impedance), QRS amplitude, or QRS morphology.

According to embodiments of the present invention, the device further comprises a posture sensor configured to sense a posture of the patient and/or an activity sensor is configured to sense an activity level of the patient.

According to embodiments of the present invention, the control module is configured to perform a template creation procedure including: instructing the impedance measurement module to measure impedance signals in time windows in the refractory period of the left ventricle at predetermined delays relative to the onset of the refractory period of the left ventricle using at least one electrode configuration and instructing the PNS detection module to create impedance signal templates using the gathered impedance signals. The control module is configured to two or several impedance signal templates in the PNS detection.

According to embodiments of the present invention, the control module is configured to perform a template creation procedure including: instructing the pacing module to deliver at least one pacing pulse having a predetermined pulse amplitude and/or width in at least one time window within a refractory period of the left ventricle during a number of cardiac cycles for at least one posture, wherein pacing pulses are repeatedly delivered during a number of cardiac cycles, instructing the impedance measurement module to measure impedance signals in time windows synchronized with the delivery of pacing pulses in the refractory period of the left ventricle using at least one electrode configuration; and instructing the PNS detection module to: gather impedance signals measured within the time windows of the cardiac cycles for the different postures and create signal templates for the at least one posture using the gathered impedance signals. The control module is configured to use two or more impedance signal templates in the PNS detection.

According to embodiments of the present invention, the control module is configured to perform a template creation procedure including: instructing the pacing module to deliver at least one pacing pulse having a predetermined pulse amplitude and/or width in at least one time window within a refractory period of the left ventricle during a number of cardiac cycles at different activity levels, wherein pacing pulses are repeatedly delivered during a number of cardiac cycles, instructing the impedance measurement module to measure impedance signals in time windows synchronized with the delivery of pacing pulses in the refractory period of the left ventricle using at least one electrode configuration and instructing the PNS detection module to: gather impedance signals measured within the time windows of the cardiac cycles for at least the different activity levels and create impedance signal templates for each activity level using the gathered impedance signals. The control module is configured to use two or more impedance signal templates in the PNS detection.

According to embodiments of the present invention, the control module is configured to perform a template creation procedure including: instructing the pacing module to deliver at least one pacing pulse having a predetermined pulse amplitude and/or width in at least one time window within a refractory period of the left ventricle during a number of cardiac cycles using different electrode configurations, wherein pacing pulses are repeatedly delivered during a number of cardiac cycles, instructing the impedance measurement module to measure impedance signals in time windows synchronized with the delivery of pacing pulses in the refractory period of the left ventricle using at least one electrode configuration, and instructing the PNS detection module to: gather impedance signals measured within the time windows of the cardiac cycles, and create impedance signal templates for each electrode configuration using the gathered impedance signals. The control module is configured to use two or more impedance signal templates in the PNS detection.

According to embodiments of the present invention, the PNS detection module is configured to: receive a verification whether a PNS has occurred or not during the gathering of impedance signals, the verification being received from an extracorporeal unit via a communication module of the implantable medical device, and determine whether a created impedance signal template is a template with PNS content or without PNS content depending on the received verification.

According to embodiments of the present invention, the PNS detection module is configured to, during a template creation procedure, analyze the gathered impedance signals to determine whether a PNS has occurred or not including: for each time window, calculating the frequency content of the impedance waveform, determining a frequency content related to respiration, detecting that a PNS has occurred if the frequency content related to respiration is above a predetermined frequency content threshold for a selected frequency range, and determining whether a created impedance signal template is a template with PNS content or without PNS content depending on whether a PNS was detected or not.

According to embodiments of the present invention, the control module is configured to, at regular intervals and/or at detection of a specific posture and/or a specific activity level and/or at occurrence of a predetermined hemodynamic event, perform a PNS test including: instructing the pacing module to deliver a pacing pulse having a predetermined pulse amplitude and/or width within a refractory period of the left ventricle, wherein pacing pulses are repeatedly delivered during a number of cardiac cycles, instructing the impedance measurement module to measure impedance signals in time windows synchronized with the delivery of pacing pulses in the refractory period of the left ventricle using at least one electrode configuration, and instructing the PNS detection module to: gather at least one measured impedance signal from each time window, and analyze the gathered impedance signals to detect morphological events and/or deviations indicating PNS by comparing the gathered impedance signals with an impedance signal template.

According to embodiments of the present invention, the control module is configured to instruct the PNS detection module to: gather at least one measured impedance signal from each time window, and analyze the gathered impedance signals to identify a first pulse amplitude and/or width above the pacing therapy threshold that do not cause PNS. The control module is configured to determine an adequate PNS threshold gap to be the difference between the identified pulse amplitude and/or width and the pacing therapy threshold.

According to embodiments of the present invention, the control module is configured to initiate a PNS threshold test including instructing the pacing module to deliver a pacing pulse within a refractory period of the left ventricle of the heart, wherein pacing pulses are repeatedly delivered during a number of cardiac cycles and wherein the pacing pulses having a successively changed pulse amplitude and/or width, and instructing the impedance measurement module to measure impedance signals in time windows synchronized with the delivery of pacing pulses in the refractory period of the left ventricle using at least one electrode configuration, and instructing the PNS detection module to: gather at least one measured impedance signal from each time window, and analyze the gathered impedance signals to detect morphological events and/or deviations indicating PNS by comparing the gathered impedance signals with impedance signal templates to identify pulse amplitudes and/or widths that do not cause PNS. The control module is configured to determine the maximum of the pulse amplitude and/or width that do not cause PNS to be a PNS threshold.

According to embodiments of the present invention, the control module is configured to determine a PNS threshold gap between a PNS threshold and a pacing therapy threshold, wherein the control module is configured to, at a PNS threshold gap being below a predetermined value, perform an adaptation of pacing settings.

According to embodiments of the present invention, the control module is configured to, at detection of PNS at pulse amplitudes and/or widths below a predetermined threshold for a specific electrode configuration instruct the pacing module to change electrode configuration for delivery of pacing pulses and/or adapt pulse amplitudes and/or widths.

According to embodiments of the present invention, the control module is configured to search for another electrode configuration including selection of an electrode configuration according to a predetermined order of a set of configurations for delivery of pacing pulses, instruct the pacing module to deliver a pacing pulse having a predetermined pulse amplitude and/or width within a refractory period of the left ventricle during a number of cardiac cycles, wherein pacing pulses are repeatedly delivered during a number of cardiac cycles, for each of the electrode configurations, instruct the impedance measurement module to measure impedance signals in time windows synchronized with the delivery of pacing pulses in the refractory period of the left ventricle using at least one electrode configuration, and instruct the PNS detection module to: gather impedance signals measured within the time windows of the cardiac cycles and analyze the gathered impedance signals to detect morphological events or deviations indicating PNS by comparing the gathered impedance signals with impedance signal templates. The control module is configured to select the electrode configuration for pacing stimulation that provides a predetermined PNS threshold gap.

According to embodiments of the present invention, templates without PNS content are used in the PNS detection. In that case, the PNS detection module is, when analyzing the gathered impedance signals to detect PNS, configured to: for each time window, subtract each impedance sample from a corresponding impedance sample of a selected impedance signal template to obtain difference values (which preferably are absolute), process the absolute difference values to create an aggregated value for the time windows, compare the aggregated value with a predetermined limit based on the template, and detect that a PNS has occurred if the aggregated value is above the predetermined limit.

According to other embodiments of the present invention, templates with PNS content are used in the PNS detection. In that case, the PNS detection module is, when analyzing the gathered impedance signals to detect PNS, configured to, for each time window, subtract each impedance sample from a corresponding impedance sample of a selected impedance signal template to obtain difference values (which preferably are absolute), process the absolute difference values to create an aggregated value for the time windows, compare the aggregated value with a predetermined limit based on the template, and detect that a PNS has occurred if the aggregated value is below the predetermined limit.

According to embodiments of the present invention templates without PNS are used and the PNS detection module is, when analyzing the gathered impedance signals to detect PNS, configured to, for each time window, cross-correlate an impedance signal during a time window with an impedance signal template for the corresponding time window to produce a first cross-correlation result, for each time window, cross-correlate an impedance signal template with itself to produce a second cross-correlation result, calculate a difference value for each time window between the first and second cross-correlation results, e.g. for the peak values of the results, calculate a sum of all absolute difference values, compare the sum with a predetermined limit value, and detect that a PNS has occurred if the aggregated value exceeds the predetermined limit value.

According to embodiments of the present invention templates with PNS are used and the PNS detection module is, when analyzing the gathered impedance signals to detect PNS, configured to, for each time window, cross-correlate an impedance signal during a time window with an impedance signal template for the corresponding time window to produce a first cross-correlation result, for each time window, cross-correlate an impedance signal template with itself to produce a second cross-correlation result, calculate a difference value for each time window between the first and second cross-correlation results, calculate a sum of all absolute difference values, compare the sum with a predetermined limit value, and detect that a PNS has occurred if the aggregated value is below the predetermined limit value.

According to embodiments of the present invention, the PNS detection module is, when analyzing the gathered impedance signals to detect PNS, configured to, for each time window, determine a number of points in the impedance waveform where a derivative of the impedance waveform shows a change of sign, wherein a new sign of the derivative lasts a predetermined period of time, and detect that a PNS has occurred if a difference between a determined number of points and a reference number of points is higher than or equal to a predetermined limit value.

According to embodiments of the present invention, the PNS detection module is, when analyzing the gathered impedance signals to detect PNS, configured to, for each time window, calculate the frequency content of the impedance waveform, compare the calculated frequency content with a frequency content of selected impedance templates, and detect that a PNS has occurred if a deviation between the calculated frequency content and the frequency content of the selected impedance templates is above a predetermined frequency content threshold for a selected frequency range.

According to embodiments of the present invention, the control module is configured to, at regular intervals and/or at detection of a specific posture and/or a specific activity level and/or at occurrence of a predetermined hemodynamic event, initiate a PNS test including instructing the pacing module to repeatedly deliver pacing pulses within a refractory period of the left ventricle of the heart during a number of cardiac cycles, the pacing pulses having a predetermined pulse amplitude and/or width, and instructing the impedance measurement module to measure impedance signals in time windows synchronized with the delivery of a pacing pulse in the refractory period of the left ventricle using more than one electrode configuration in a time window or alternately using different electrode configurations for different time windows, instructing the PNS detection module to gather at least one measured impedance signal from each time window and for each electrode configuration, and analyze the gathered impedance signals to detect morphological events and/or deviations indicating PNS by comparing the gathered impedance signals for each electrode configuration with a corresponding impedance signal template for each electrode configuration and applying an PNS factor for each electrode configuration.

According to embodiments of the present invention, the PNS detection module is, so as to detect morphological events and/or deviations indicating PNS, configured to calculate a difference waveform between a measured impedance waveform and each corresponding template for each electrode configuration, determine a difference value for each electrode configuration, multiply each difference value with the corresponding PNS factor to determine a resulting value for each electrode configuration, add the resulting values for all electrode configurations, and detect that PNS has occurred if the added resulting value is higher than a predetermined PNS threshold.

According to embodiments of the present invention, the phrenic nerve stimulation, PNS, detection module is configured to calculate a PNS factor for each electrode configuration as reflecting a difference between an impedance signal template with PNS content and an impedance signal template without PNS content for that specific electrode configuration.

According to embodiments of the present invention, the control module is configured to instruct the pacing module to deliver pacing pulses having predetermined energies within a refractory period of the left ventricle, wherein pacing pulses are repeatedly delivered during a number of cardiac cycles, wherein the impedance measurement module is configured to measure impedance signals in time windows synchronized with the delivery of pacing pulses in the refractory period of the left ventricle using more than one electrode configuration simultaneously or alternately using different electrode configurations for different time windows. The PNS detection module is configured to gather at least one impedance signal from each time window and for each electrode configuration, calculating a PNS factor for each electrode configuration reflecting a difference between frequency content in an impedance waveform with PNS content and frequency content in an impedance waveform without PNS content.

Further objects and advantages of the present invention will be discussed below by means of exemplifying embodiments.

These and other features, aspects and advantages of the invention will be more fully understood when considered with respect to the following detailed description, appended claims and accompanying drawings.

BRIEF DESCRIPTION OF THE DRAWINGS

The drawings are not necessarily drawn to scale and illustrate generally, by way of example, but no way of limitation, various embodiments of the present invention. Thus, exemplifying embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. For example, embodiments may be used with a pacemaker, a cardioverter, a defibrillator, and the like.

Systems, devices and methods according to the present invention may include one or more of the features, structures, methods, or combinations thereof described herein. For example, a device or system may be implemented to include one or more of the advantageous features and/or processes described below in various different embodiments. It is intended that such a device or system need not include all of the features described herein, but may be implemented to include selected features that provide for useful structures and/or functionality. Such a device or system may be implemented to provide a variety of therapeutic or diagnostic functions.

A wide variety of implantable monitoring and/or stimulation devices may be configured to implement phrenic nerve stimulation detection and phrenic nerve stimulation reduction according to the present invention. A non-limiting representative list of such devices includes cardiac monitors, pacemakers, cardioverters, defibrillators, resynchronizers, and other cardiac monitoring and therapy delivery devices. These devices may be configured with different electrode arrangements including transvenous, endocardial, and epicardial electrodes. In multi-electrode pacing systems, multiple electrodes may be disposed in a single heart chamber, in multiple heart chambers, and/or elsewhere in a patient's body. Typically, pacing energy is delivered to the heart via cathode electrode(s) at one or more pacing sites, with a return path provided via anode electrode(s). If cardiac capture occurs, the injected energy creates a propagating wavefront of depolarization to trigger a contraction of the cardiac muscle.

Figure 1:
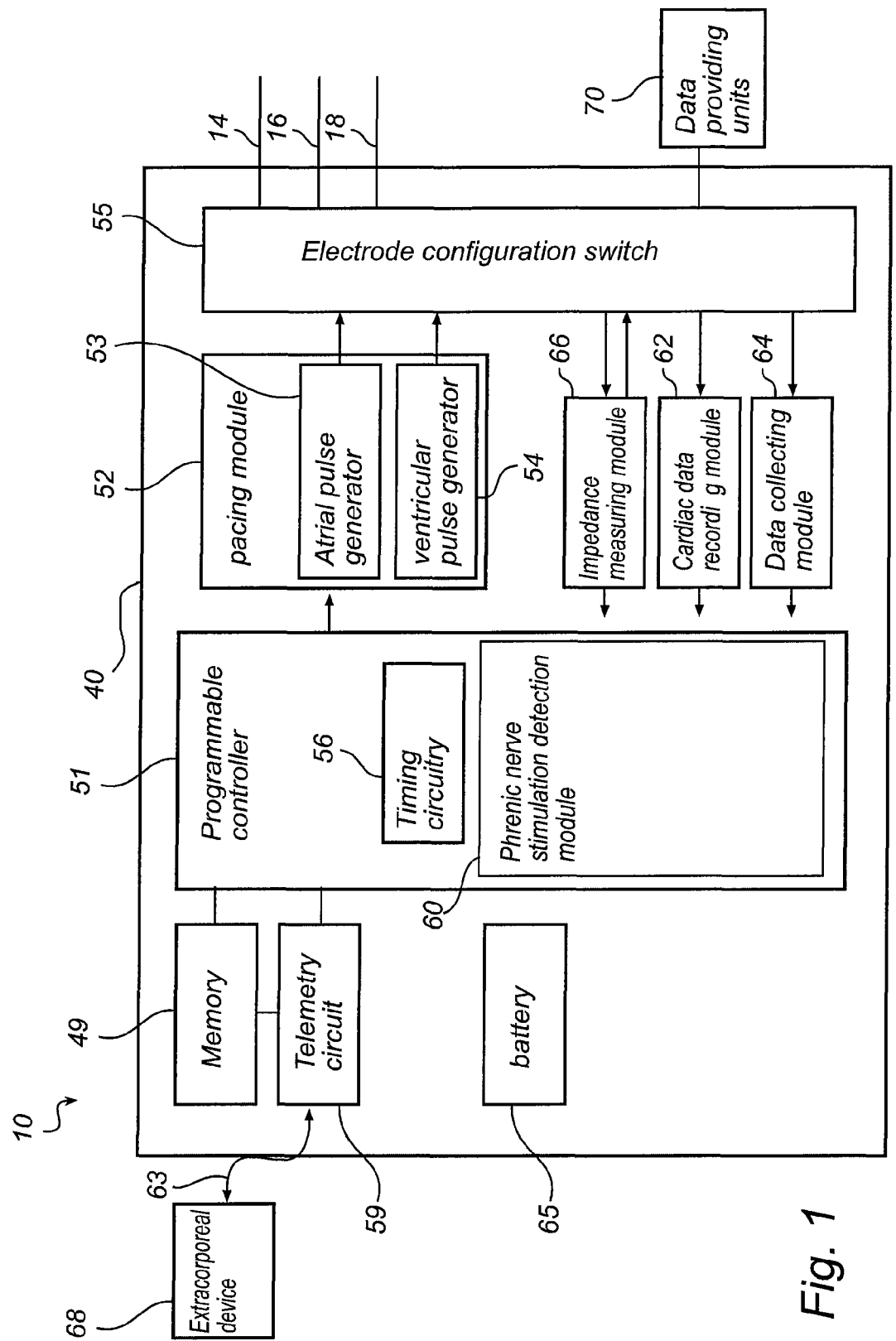
FIG. 1 is a simplified functional block diagram of one embodiment of an implantable medical device in accordance with the present invention, illustrating basic elements of the system.

In FIG. 1, an exemplary, simplified block diagram depicting various components of the cardiac stimulator according to embodiments of the present invention is shown. The cardiac stimulator 10 is capable of delivering cardiac therapy via different electrode pairs and is configured to integrate both monitoring and therapy features, as will be described below. Further, the cardiac stimulator 10 is capable of collecting and processing data about the heart 12 (see FIG. 2) from electrode pairs for sensing cardiac electrogram (EGM) signals and/or intracardiac or transthoracic impedance. While a particular multi-chamber device is shown, it is to be appreciated and understood that this is done for illustration purposes only. Thus, the techniques and methods described below can be implemented in connection with any suitable configured or configurable stimulation device. Accordingly, one of skill in the art could readily duplicate, eliminate, or disable the appropriate circuitry in any desired combination to provide a device capable of treating the appropriate chamber with pacing stimulation.

The cardiac stimulator 10 has a housing 40, often referred to as the "can" or "case electrode". The housing 40 may function as a return electrode in "unipolar" modes. Further, the housing 40 includes connector (not shown) having a plurality of terminals (not shown) for connection with electrodes and/or sensors.

The cardiac stimulator 10 includes a programmable microcontroller or control module 51 that inter alia controls the various modes of stimulation therapy. As is well known within the art, the microcontroller 51 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 51 includes the ability to process or monitor input signals (data or information) as controlled by a program stored in a designated block of memory. The type of microcontroller is not critical to the described implementations. Rather, any suitable microcontroller 51 may be used that carries out the functions described herein. The use of micro-processor based control circuits for performing timing and data analysis are well known in the art.

Figure 2:
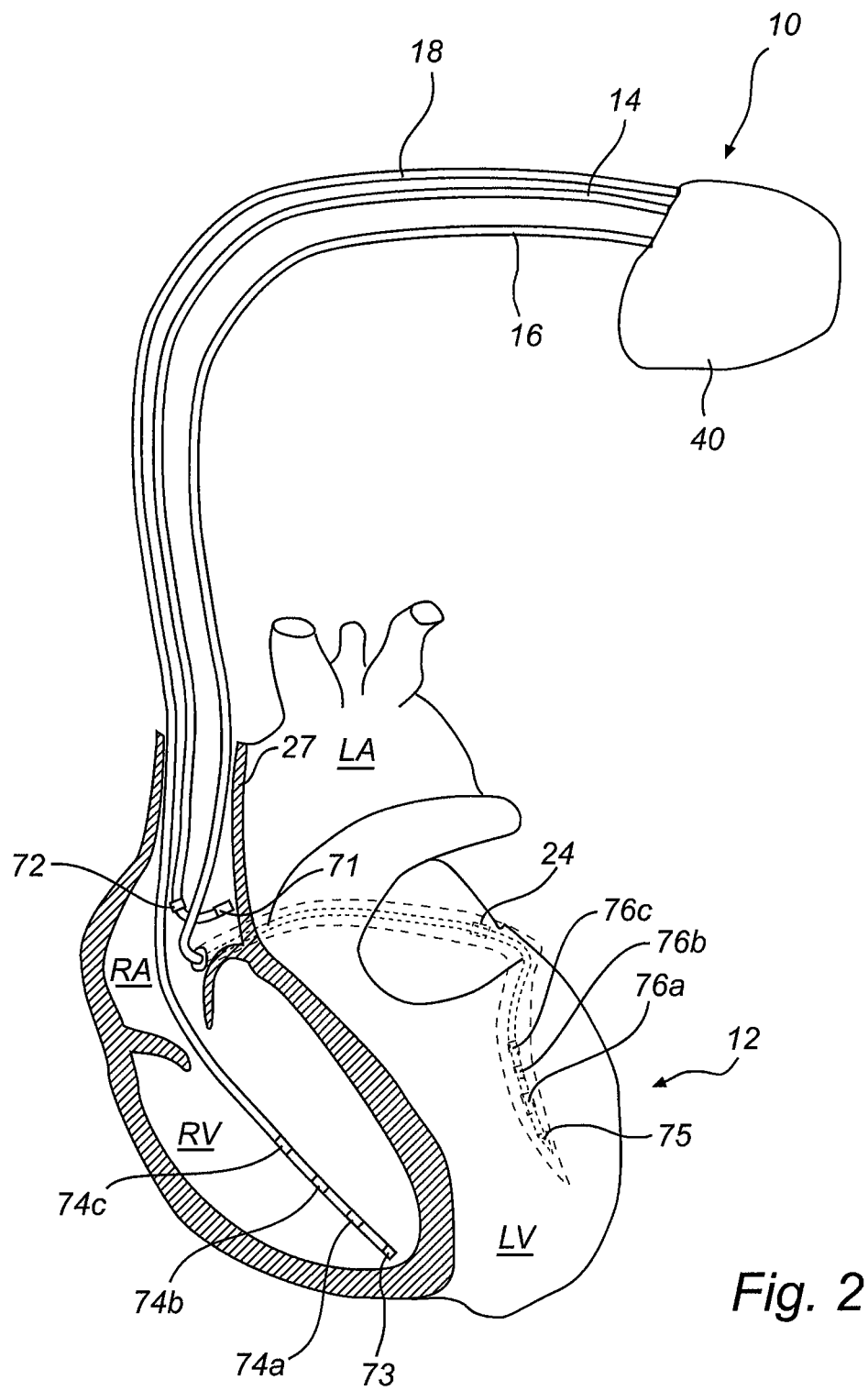
FIG. 2 is a simplified and schematic diagram of one embodiment of a system configuration according to the present invention including an implantable stimulation device in electrical communication with several leads implanted in a patient's heart for detecting cardiac activity and for delivering multi-chamber stimulation.

Furthermore, the cardiac stimulator 10 includes pacing module 52 adapted to provide pacing signals for delivery to the patient. The pacing module 52 comprises an atrial pulse generator 53 and a ventricular pulse generator 54 that generate pacing stimulation pulses for delivery by leads 14, 16, and 18 via an electrode configuration switch 55. In FIG. 2, an embodiment including a right atrial lead 14, a coronary sinus lead 16, and a right ventricular lead 18 is shown.

It is understood that in order to provide stimulation therapy in each of the four chambers, the atrial and ventricular pulse generators 53 and 54, may include dedicated, independent pulse generators, multiplexed pulse generators, or shared pulse generators. The pulse generators 53 and 54 are controlled by the microcontroller 51 via appropriate control signals to trigger or inhibit stimulation pulses.

A cardiac data recording module 62 is configured to collect, for example, cardiac signals such as IEGM signals and, if required, record the cardiac signals. The cardiac data recording module 62 may for this purpose interact with an ECG unit (not shown) that provides electrical impulses or other observed signals that can be used to, for example, monitor the patient's ECG waveform. Based on the IEGM signals, the onset of the refractory period of the left ventricle can be determined, which information can be used in the PNS detection.

A data collecting module 64 is configured to collect measurement condition information corresponding to, for example, activity level information of the patient and/or body posture information.

The data collecting module 64 suitably interacts with one or more data providing units or sensors 70 to obtain data about the patient such as activity level or body posture. The data providing units 70 include, for example, an accelerometer.

An impedance measuring module 66 is configured to measure, for example, intracardiac impedance and/or transthoracic impedance via electrodes of the medical leads 14, 16, and 18 and/or the can. The impedance measuring module 66 may comprise a voltage measuring circuit (not shown) for measuring a voltage via the electrode configuration switch 55 and electrodes arranged in the medical leads (e.g. over LV tip electrode 75 and LV ring electrode 76a or over LV ring electrodes 76b and 76c, see FIG. 2).

Further, the impedance measuring module 66 may also include a current injection circuit (not shown) for injecting current via the electrode configuration switch 55 and electrodes arranged in the medical leads (e.g. over LV tip electrode 75 and LV ring electrode 76a or over LV ring electrodes 76b and 76c, see FIG. 2).

Control signals from the microcontroller 51 determine, for example, when the cardiac data recording module 62 and/or data collecting module 64 and/or impedance measuring module 66 collects signals, stores them in the memory or transmit them to a phrenic nerve stimulation, PNS, detection module 60.

The cardiac data recording module 62 and the impedance measuring module 66 are coupled to the right atrial lead 14, the coronary sinus lead 16, and the right ventricular lead 18 to sample cardiac signals across any combination of electrodes.

The microcontroller 51 includes timing control circuitry 56 to control timing of the stimulation pulses (e.g. pacing rate, AV delay, VV delay, etc.) as well as to keep track of timing of refractory periods blanking intervals, etc., which is well known in the art. In addition, the microcontroller 51 may include components such as e.g. an arrhythmia detector (not shown). Furthermore, the timing control circuitry 56 controls the selection of electrode configuration, i.e. pacing sites, used for delivering the stimulation pulses.

Furthermore, the microcontroller 51 is coupled to a memory 49 by a suitable data/address bus (not shown), wherein the programmable operating parameters used by the microcontroller 51 are stored and modified, as required, in order to customize the operation of the cardiac stimulator to the needs of a particular patient. Such operating parameters define, for example, pacing pulse amplitude, pulse duration, etc.

Advantageously, the operating parameters may be non-invasively programmed into the memory 49 through a communication module 59 including, for example, a telemetry circuit for telemetric communication via communication link 63 with an external device 68, such as a programmer or a diagnostic system analyzer. The telemetry circuit 59 advantageously allows intracardiac electrograms and status information relating to the operation of the device 10 to be sent to the external device 68 through an established communication link 63. Further, the communication module may alternatively or as a complement to the telemetry circuit include circuits for RF communication.

Moreover, the cardiac stimulator 10 additionally includes a battery 65 that provides operating power to all of the circuits shown in FIG. 1. Preferably, the stimulator 10 employs lithium or similar battery technology.

The PNS detection module 60 is configured to detect PNS by analyzing excursions or deviations of impedance signals caused by PNS. The excursions or deviations are identified in recorded impedance signals by comparison with templates, preferably different templates for different postures and/or activity levels of the patient as well as for different measurement vectors. Further, templates with PNS content as well as templates without any PNS content may be used in the PNS detection.

Figure 4:
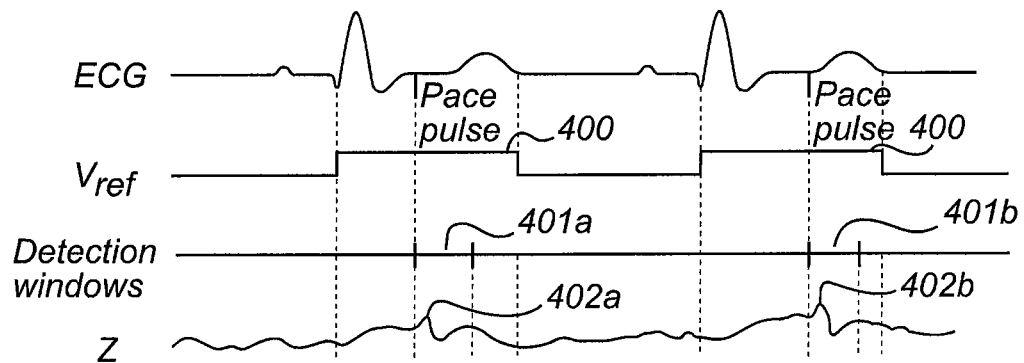
FIG. 4 schematically illustrates various waveforms including ECG and impedance waveforms with PNS content during successive cardiac cycles.
Figure 4:
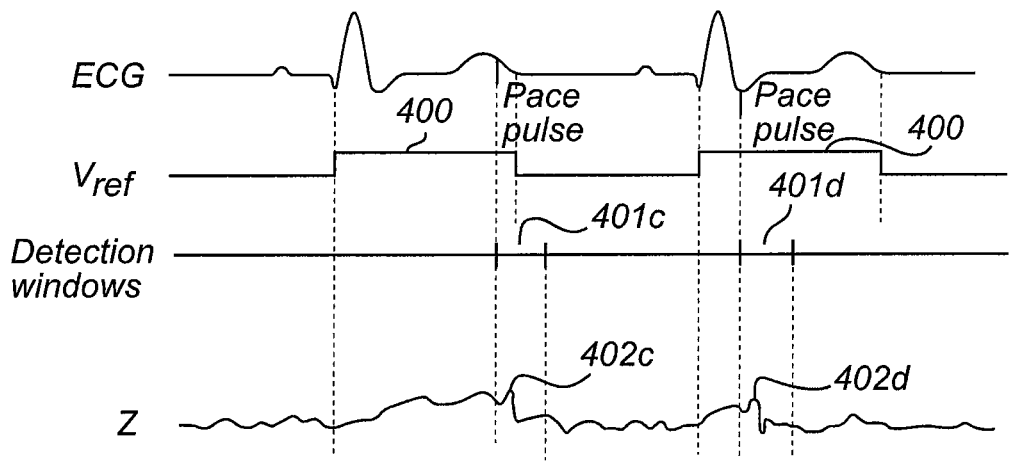

The present invention is based on the insight that the PNS caused excursion or deviation moves in time in synchronism with the stimulation pulse delivered to the left ventricle, which can be utilized to increase the accuracy of the PNS detection. The pace pulses are delivered to the left ventricle inside the refractory period of the left ventricle. Simultaneously with the stimulation pulse a time window is started that is broad enough to capture the PNS caused excursions or deviations. Further, the stimulation pulses are delivered with different timings relative to the onset of the refractory period of the left ventricle and since the time windows are synchronized with the stimulation pulses, the time windows will move from beat to beat relative to the onset of the refractory period of the left ventricle. The impedance signals are recorded within the time windows and are collected beat by beat. This is illustrated in FIG. 4 and is discussed in more detail below.

The aforementioned component or components of the microcontroller 51 may be implemented as part of the microcontroller 51, or as software/firmware instructions programmed into the device and executed on the microcontroller 51 during certain modes of operation.

With reference to FIG. 2, one implementation of a system according to the present invention including an implantable cardiac stimulator as described in FIG. 1 connectable to one or more medical leads will be discussed. As the skilled person realizes, the system implementation shown in FIG. 2 is only exemplary.

The implantable cardiac stimulator 10 is in electrical communication with a patient's heart 12 by way of three leads 14, 16, and 18 suitable for delivering multi-chamber stimulation therapy.

To sense atrial signals and to provide right atrial chamber stimulation therapy, the stimulator 10 is coupled to an implantable right atrial lead 14 having, for example, an atrial tip electrode 71, which typically is implanted in the patient's right atrial appendage or septum. FIG. 2 shows the right atrial lead 14 as also having an atrial ring electrode 72.

The cardiac stimulator 10 is in electrical communication with the heart 12 by way of an implantable right ventricular lead 18 having, in this embodiment, a right ventricular tip electrode 73 and right ventricular ring electrodes 74a-74c. Typically, the right ventricular lead 18 is transvenously inserted into the heart 12 to place the right ventricular tip electrode 73 in the right ventricular apex. The right ventricular lead 18 is capable of sensing or receiving cardiac signals, and delivering stimulation in the form of pacing therapy.

The cardiac stimulator 10 may further sense left atrial and ventricular cardiac signals and provide left chamber pacing therapy via the coronary sinus lead 16 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible via the coronary sinus.

The coronary sinus lead 16 is designed to receive atrial and ventricular pacing signals and to deliver left ventricular pacing therapy using, for example, a left ventricular tip electrode 75 and left ventricular ring electrodes 76a-76c, and deliver left atrial pacing therapy using a left atrial ring electrode 24.

In operation, the cardiac stimulator 10 obtains data about the heart 12 via the leads 14, 16 and 18 and possibly via other data providing units. This data is provided to the internal processor 51 (see FIG. 1), which analyses the data and provides a response as appropriate. In particular, the cardiac stimulator 10 generates one or more therapy signals that are preferably optimized in accordance with the obtained data.

Figure 3:
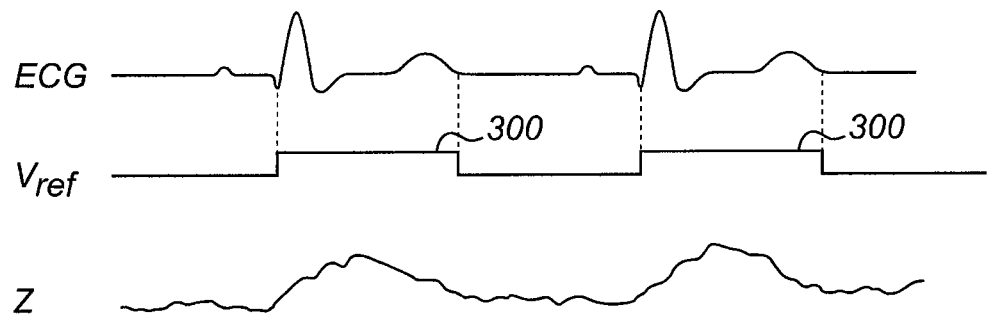
FIG. 3 schematically illustrates various waveforms including ECG and impedance waveforms without PNS content during successive cardiac cycles.

As has been discussed above, left ventricular pacing via the left ventricular lead 16, placed via the coronary sinus, using the electrodes 75, 76a-76c, may cause undesired phrenic nerve stimulation due to the proximity of the coronary veins to the phrenic nerve. Unintended activation of the phrenic nerve via a cardiac pacing pulse can be uncomfortable for the patient, and can interfere with breathing. Therefore, phrenic nerve activation from cardiac pacing may cause the patient to exhibit uncomfortable breathing patterns timed with left ventricular pace. In FIGS. 3 and 4, respectively, the impedance signal morphology following a ventricular pace without PNS (FIG. 3) and with PNS (FIG. 4) is schematically illustrated.

In FIG. 3, an impedance signal, Z, without any undesired phrenic nerve stimulation is illustrated over two consecutive cardiac cycles. As can be seen, the impedance signal, Z, varies with the ECG signal. The refractory period 300 for the left ventricle, $V_{ref}$, is shown for the successive cardiac cycles. As can be seen in FIG. 4, the impedance signal Z will demonstrate significant morphological excursions or deviations caused by the PNS compared to the non-PNS impedance signal shown in FIG. 3. Hence, if a PNS has occurred there exist PNS footprints in the impedance signals that can be used for the PNS detection.

In FIG. 4, the principles of the present invention including delivery of a pacing pulse in the refractory period of the left ventricle, recording the impedance in a time window following the pacing pulse and displacing the time windows relative each other in different cardiac cycles are shown. In this illustrated example, the pacing pulse is delivered in the refractory period of the left ventricle and the impedance signal is recorded in time windows of four consecutive cardiac cycles. However, it is not necessary to use consecutive cardiac cycles for the phrenic nerve stimulation detection, for example, every second cardiac cycle or every third cardiac cycle may instead be used.

In this illustrated case, pace pulses are delivered to the left ventricle in the refractory period 400 of the left ventricle. The delivery of each pace pulse initiates a respective time window 401a-401d having a length of about 100-150 ms and the impedance signal is recorded within these time windows. In the illustrated example, the delivery of a pace pulse triggers a phrenic nerve stimulation, which is reflected in the impedance signal by the irregularities or peaks 402a-402d. According to the present invention, the impedance signals of the time windows can be aggregated, for example, a sum impedance signal or an average impedance signal can be created to improve the detection of the phrenic nerve stimulation footprint in the impedance signal.

With reference now to FIG. 5-9, different approaches for creating templates will be discussed.

Figure 5:
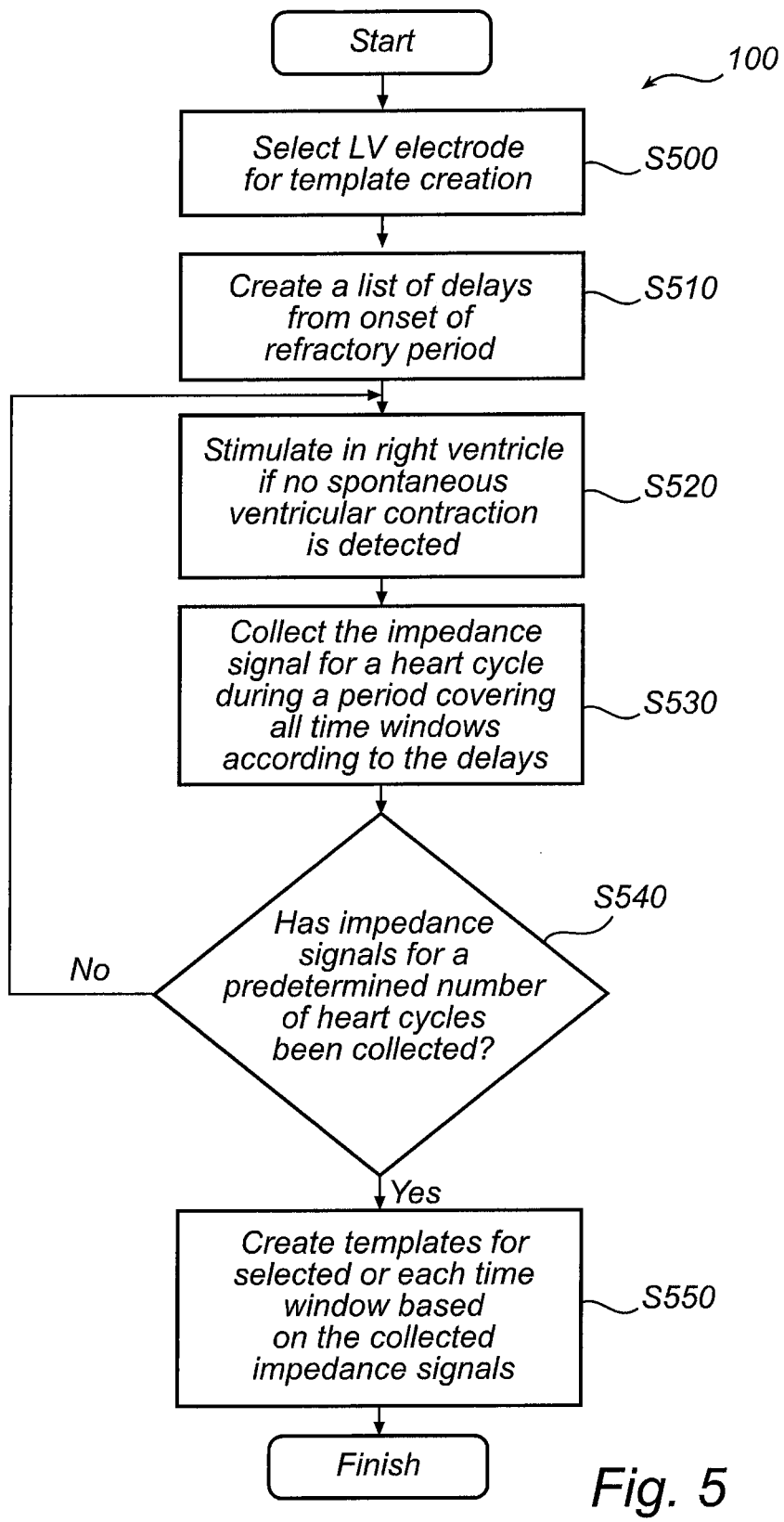
FIG. 5 is a flow chart illustrating steps in a method for creating templates without PNS content.
Figure 8:
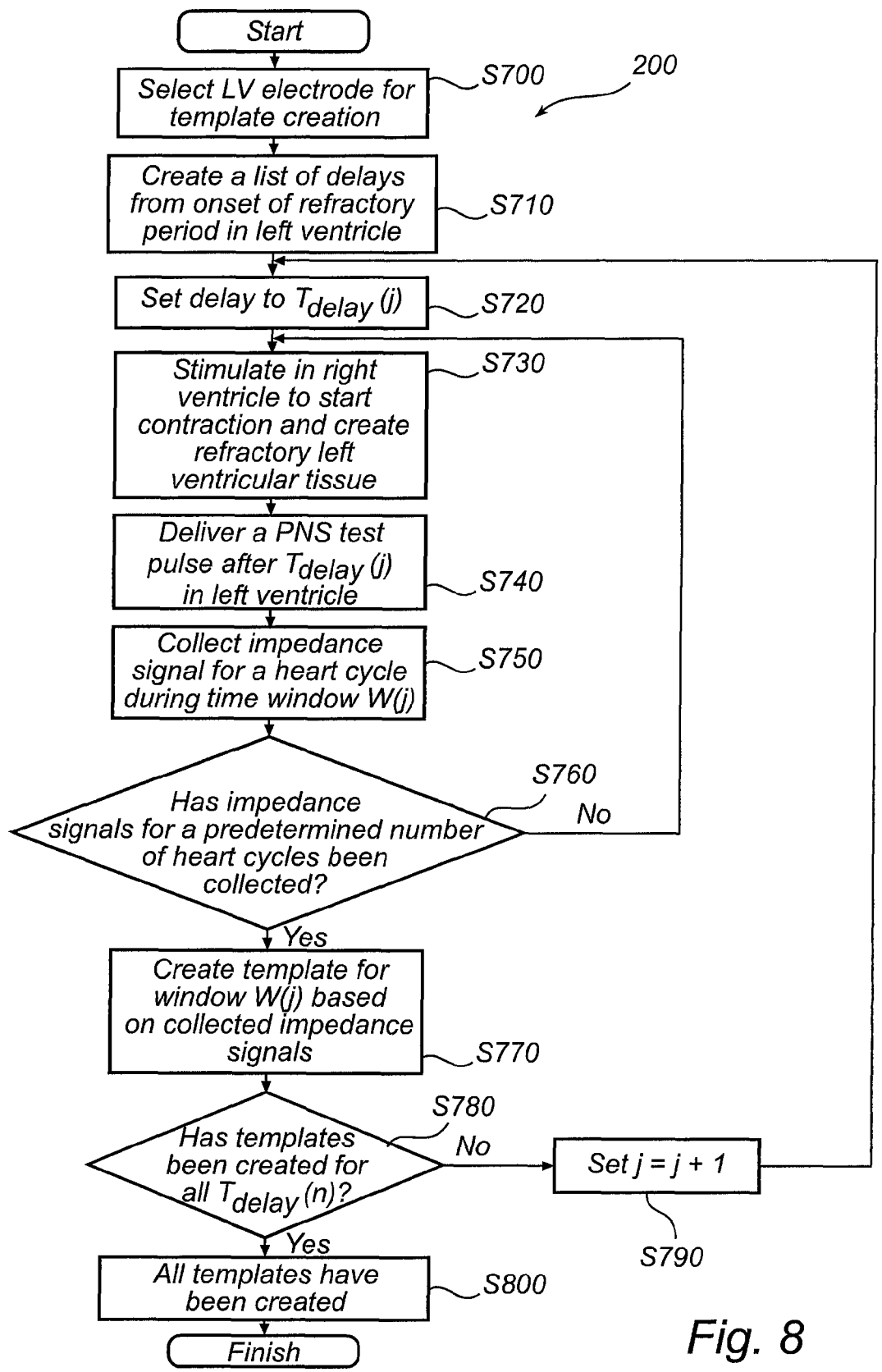
FIG. 8 is a flow chart illustrating steps in a method for creating templates with PNS content.

FIGS. 5 and 8 are flow diagrams of processes according to embodiments of the present invention. The various tasks performed in connection with the processes may be performed by software, hardware, firmware, or any combination thereof. For illustrative purposes, the following description of the processes refers to elements mentioned above in connection with FIGS. 1 and 2. In practical embodiments, portions of the processes may be performed by different elements of the described cardiac stimulator. It should be appreciated that the processes may include any number of additional or alternative tasks or steps, the tasks shown in FIGS. 5 and 8 need not be performed in the illustrated order, and the processes may be incorporated into a more comprehensive procedure or process having additional functionality not described in detail herein.

Figure 6:
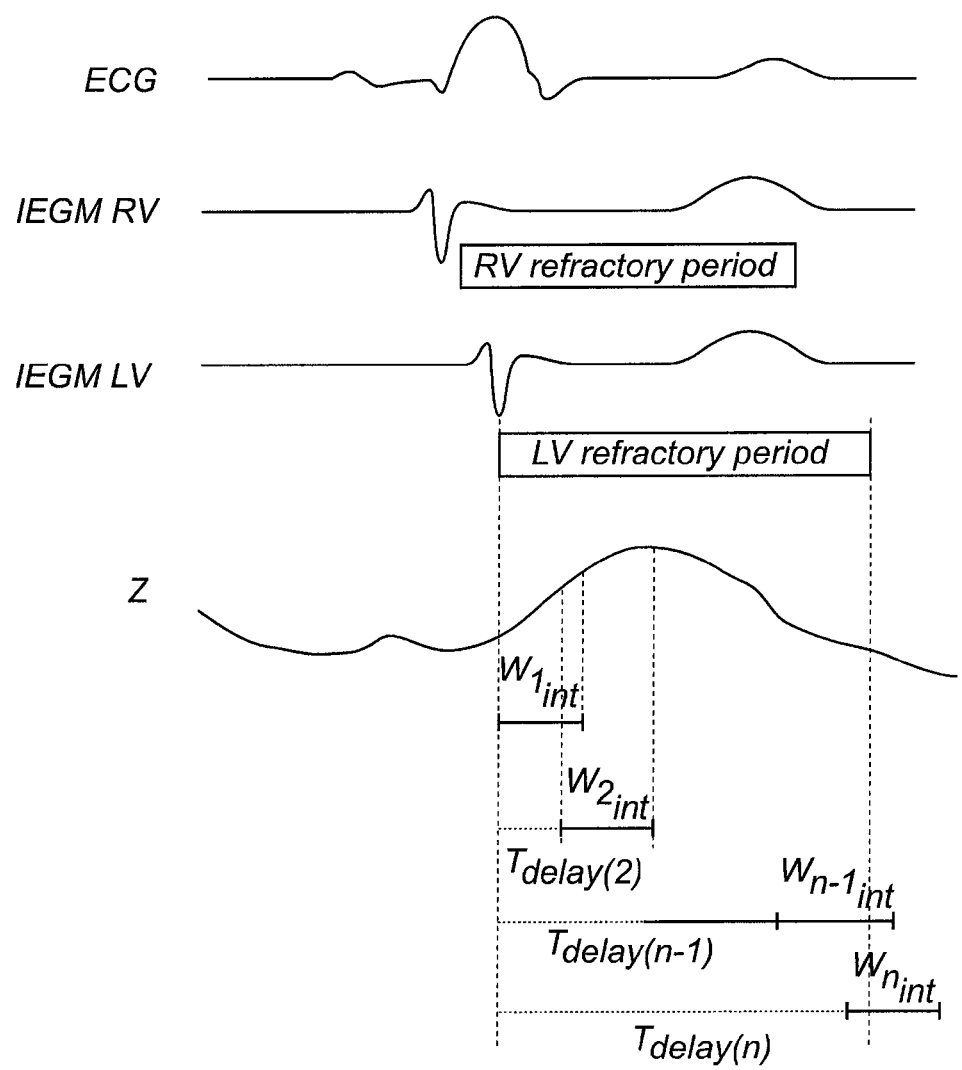
FIG. 6 schematically illustrates ECG, IEGM and impedance signals during a template creation procedure for creating templates without PNS content using stimulation.
Figure 7:
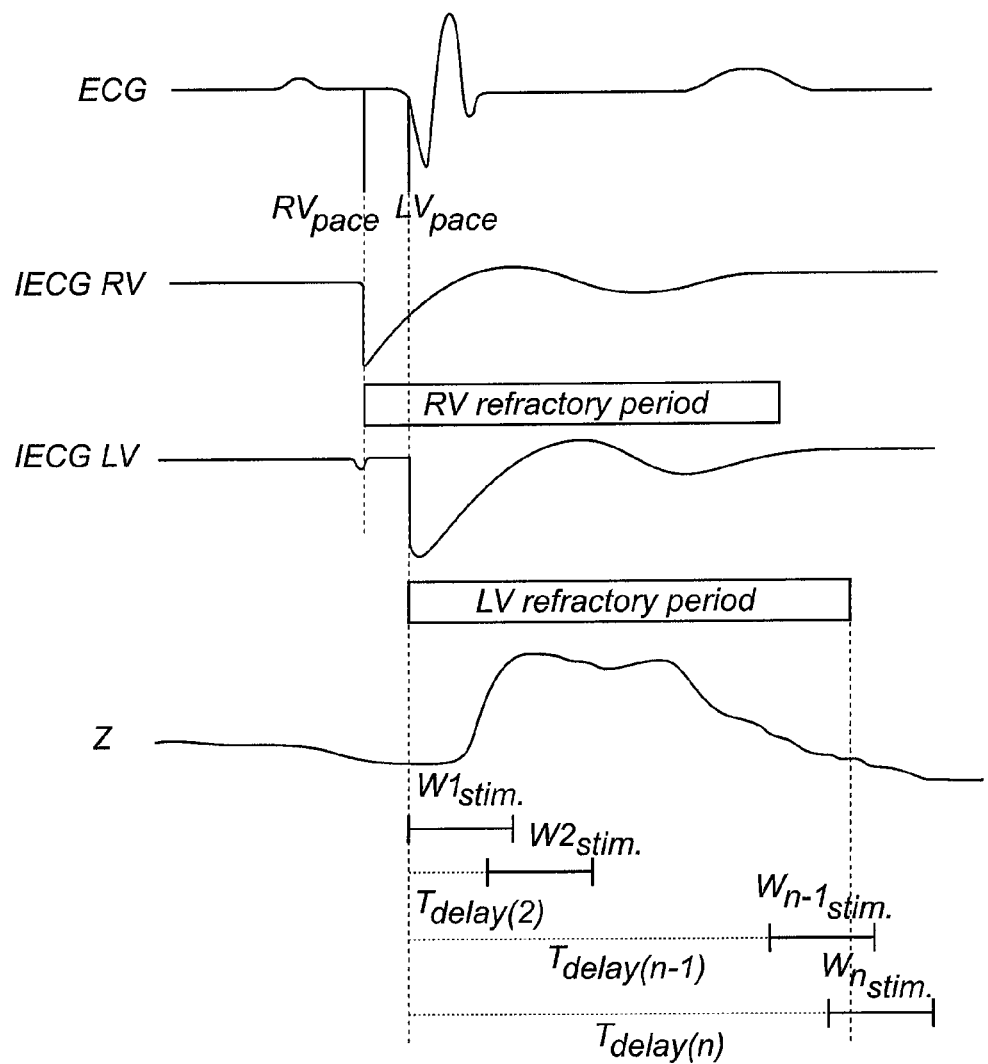
FIG. 7 schematically illustrates ECG, IEGM and impedance signals during a template creation procedure for creating templates without PNS content using stimulation based on intrinsic ventricular contractions.

With reference first to FIGS. 5-7, acquisition of templates without PNS content will be discussed. In FIG. 5, a flow chart describing steps executed when acquiring templates without PNS content is shown and in FIGS. 6 and 7 signals and time windows used for the creation of templates without PNS content are schematically illustrated. The atrial contraction may be intrinsic or pace activated. The illustrated situation concerns a patient having left bundle block, which can be seen from a broadened QRS-complex and a delay between the right ventricle and left ventricle.

In FIGS. 6 and 7, a number of possible time windows $W1_{int}$-$Wn_{int}$, for template creation within the left ventricle's refractory period are shown. Each time window will have a template, created from corresponding time windows from several cardiac cycles, for example, an average over several cardiac cycles. Further, a template is additionally preferably created for each posture and activity level. The templates can be created based on impedance measurements during a left ventricle refractory period following an intrinsic left ventricle activation or following a delivery of a stimulation pulse as shown in FIG. 6 and FIG. 7, respectively.

In order to create the template without PNS content according to this embodiment, an LV electrode for template building is first selected in step S500 of the process 100. Posture and/or activity level may also be selected or determined before the actual template creation procedure is initiated. At step S510, a list of delays, Tdelay(1)-Tdelay(n) (see FIG. 6), are created for later PNS detection using a PNS test pulse. The delays Tdelay(1)-Tdelay(n) define the starting point of the time windows $W1_{int}$-$Wn_{int}$ from the onset of the refractory period of the left ventricle, which can be initiated by an intrinsic ventricular contraction or a delivery of a stimulation pulse.

In this example, the delay Tdelay1 is zero for the first time window $W1_{int}$. Each delay is related to the first stimulation pulse (to create a ventricular contraction) or at detection of a QRS. The starting points of the windows $W1_{int}$-$Wn_{int}$ should be distributed over the left ventricular refractory period.

At step S520, the right ventricle is stimulated to start a contraction and create refractory left ventricular tissue if no spontaneous ventricular contraction is detected. Thereafter, at step S530, the impedance signal is collected during a period covering all time windows $W1_{int}$-$Wn_{int}$ following the stimulation pulse or the spontaneous contraction. Steps S520 and S530 are preferably repeated for a number of heart cycles.

Then, at step S540, it is checked whether impedance signals for a predetermined number of heart cycles have been collected. If no, the process returns to step S520. If yes, the process proceeds to step S550, where a template for selected time windows or for each time window $W1_{int}$-$Wn_{int}$ is created, for example, by extracting data from an average impedance signal based on all collected impedance signals according to the specific Tdelay and time window width.

Figure 9:
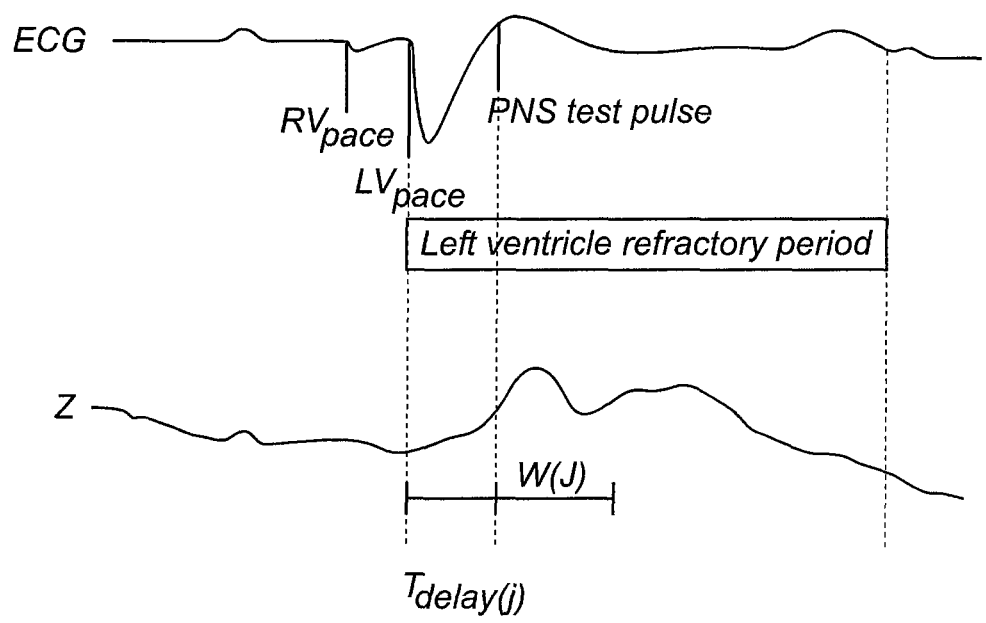
FIG. 9 schematically illustrates ECG, IEGM and impedance signals during a template creation procedure for creating templates with PNS content.

Turning now to FIGS. 8 and 9, acquisition of templates with PNS content will be discussed. In FIG. 8, a flow chart describing steps executed when acquiring templates with PNS content is shown and in FIG. 9, signals during creation of templates based on impedance signals with PNS content are schematically illustrated.

The atrial contraction may be intrinsic or pace activated. Each time window within the left ventricle refractory period will have a template, created from corresponding time windows from several cardiac cycles, for example, an average over several cardiac cycles. Further, a template is additionally preferably created for each posture and activity level. The templates can be created based on impedance measurements during a left ventricle refractory period following intrinsic left ventricle activation or following a delivery of a stimulation pulse.

In order to create the template with PNS content according to this embodiment, an LV electrode for template building is first selected in step S700 of the process 200. Posture and/or activity level may also be selected or determined before the actual template creation procedure is initiated. A pulse amplitude and/or width being sufficient for PNS should be applied in the following template creation procedure. In order to secure phrenic nerve capture, an extra margin may be added to the PNS pulse amplitude and/or width threshold.

At step S710, a list of delays, Tdelay(1)-Tdelay(n), are created for later PNS detection using a PNS test pulse. The delays Tdelay(1)-Tdelay(n) define the starting point of the time windows W(1)-W(n) from the onset of the refractory period of the left ventricle, which can be initiated by an intrinsic ventricular contraction or a delivery of a stimulation pulse.

In this example, the delay Tdelay(1) is zero for the first time window W(1). Each delay is related to the first stimulation pulse (to create a ventricular contraction) or the detection of a QRS. The starting points of the time windows W(1)-W(n) should be distributed over the left ventricular refractory period.

At step S720, a first delay(j), j=1, for the start of the time window W(j) is selected for template creation.

At step S730, a stimulation pulse in the right ventricle is delivered to start a contraction and create refractory left ventricular tissue.

Thereafter, a PNS test pulse is delivered after Tdelay(j) in the left ventricle at step S740.

At step S750, the impedance signal is collected during the time window W(j) for a heart cycle.

Thereafter, in step S760, it is checked whether impedance signals have been collected for a predetermined number of heart cycles. If no, the procedure returns to step S730. If yes, the procedure proceeds to step S770 where a template for time window W(j) is created based on the collected impedance signals during the predetermined number of heart cycles.

At step S780, it is checked whether templates have been created for all delays, Tdelay(1)-Tdelay(n), and if not, the procedure proceeds first to step S790 and then to step S720 where j is set to j=j+1, and the delay accordingly is set to Tdelay(j=j+1), respectively. Then, steps S730-S770 are repeated to create a template for the time window W(j=j+1). On the other hand, if it is verified in step S780 that a template has been created for all delays, Tdelay(1)-Tdelay(n), it is concluded in step S800 that templates for all delays Tdelay(1)-Tdelay(n) and respective time windows W(1)-W(n) have been created and the template creation process can be finished.

With reference now to FIGS. 10a-10c, and 11a-11c, analysis of impedance signal content to detect PNS will be discussed.

Figure 10A:
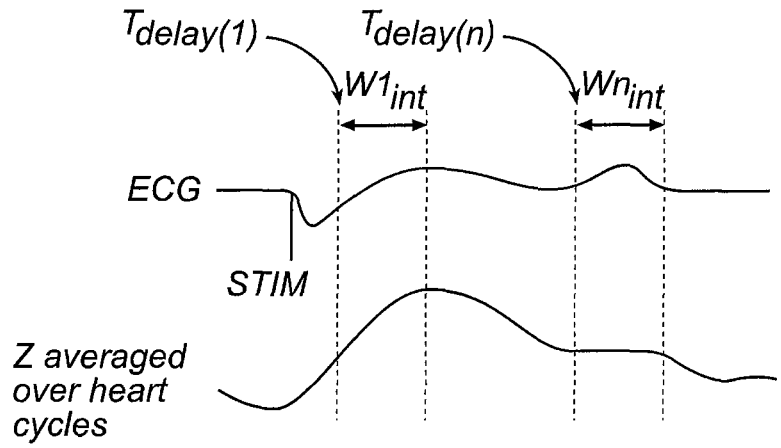
FIG. 10a-10c schematically illustrates PNS detection based on waveform comparison using templates without PNS content.
Figures 10B, 10C:
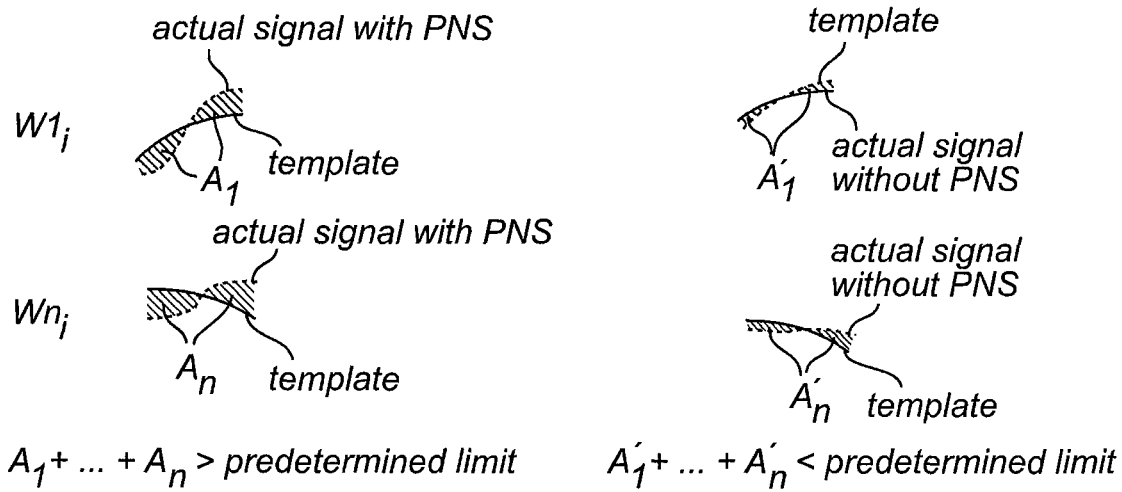
Figure 11A:
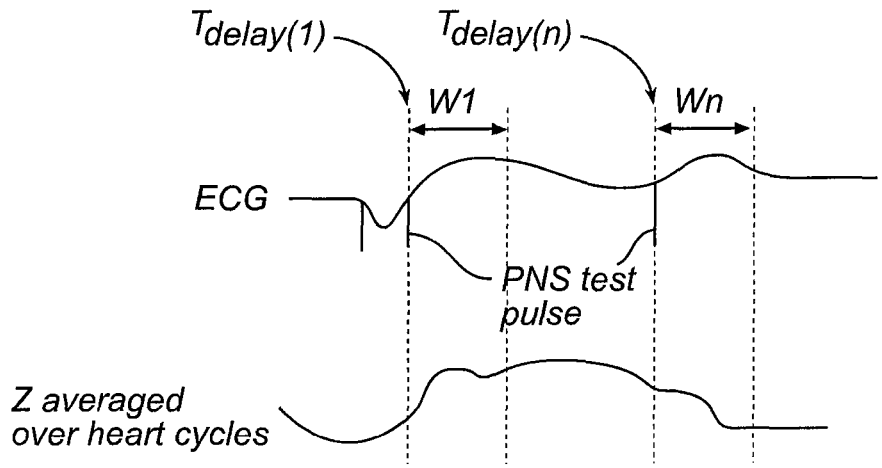
FIG. 11a-11c schematically illustrates PNS detection based on waveform comparison using templates with PNS content.
Figure 11B:
Figure 11C:

In FIGS. 10a-10c, templates without PNS content and signal comparison to detect PNS is illustrated, respectively. In FIGS. 11a-11c, templates with PNS content and signal comparison to detect PNS is illustrated, respectively. In these examples (as particularly shown in FIGS. 10b, 10c, 11b and 11c), the actual impedance signal waveforms are compared with the impedance signal waveforms of the templates to identify whether PNS is present (FIGS. 10b and 11c) or not (FIGS. 10c and 11b) in the actual impedance signals.

If templates without PNS content are used as shown in FIG. 10a-10c, a total difference area, i.e. the sum of $A_1$-$A_n$, between the actual impedance signals and the templates being larger than a predetermined limit will indicate that PNS has occurred as can be seen in FIG. 10b. However, if the total difference area, i.e. the sum of $A'_1$-$A'_n$, between the actual impedance signals and the templates is smaller than the predetermined limit it is an indication that the actual impedance signals do not include PNS content, as can be seen in FIG. 10c.

Turning now to FIG. 11a-11c where it is illustrated how the comparison may be performed when templates with PNS content are being used. In this case, a total difference area, i.e. the sum of $A_1$-$A_n$, between the actual impedance signals and the templates being larger than a predetermined limit will indicate that a PNS has not occurred, as can be seen in FIG. 11b. However, if the total difference area, i.e. the sum of $A'_1$-$A'_n$, between the actual impedance signals and the templates is smaller than the predetermined limit it is an indication that the actual impedance signals include PNS content, as can be seen in FIG. 11c.

Figure 12:
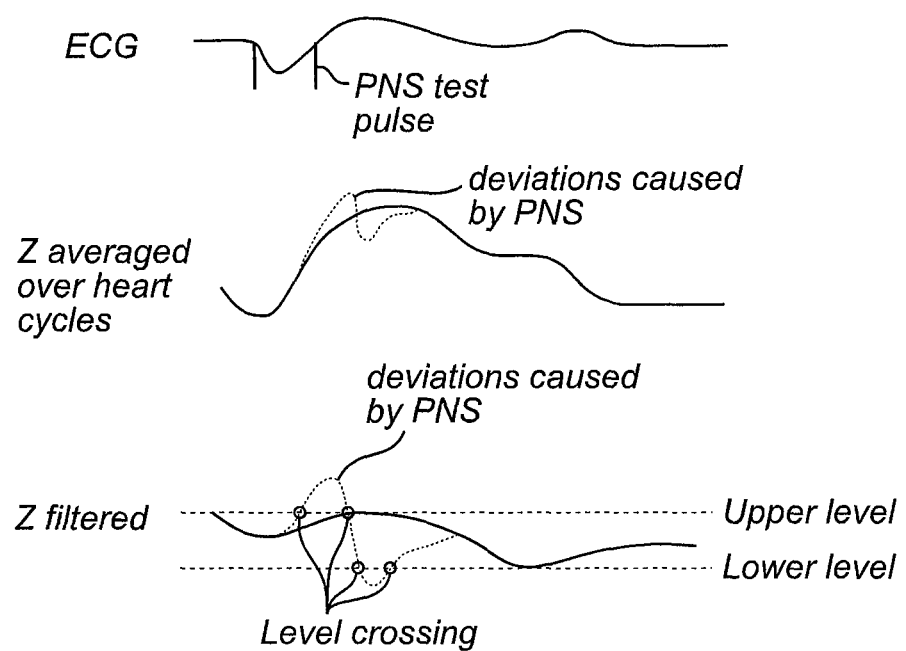
FIG. 12 schematically illustrates PNS detection based on morphology analysis.

With reference now to FIG. 12, a method for analyzing impedance morphology to identify PNS will be discussed. The effects on the impedance signals due to PNS are shown in FIG. 12 and in this example the number of times a filtered impedance signal crosses upper and lower predetermined levels is used for PNS detection. At presence of PNS, the number of level crossings will increase. As reference, the number of level crossing when no PNS is at hand and the number of level crossings at presence of PNS are counted. The predetermined upper and lower levels are set so there is a difference between the two cases. For example, if two or more level crossings occur it is determined that PNS has occurred. In FIG. 12, a PNS is detected since four level crossings are identified.

Figure 13:
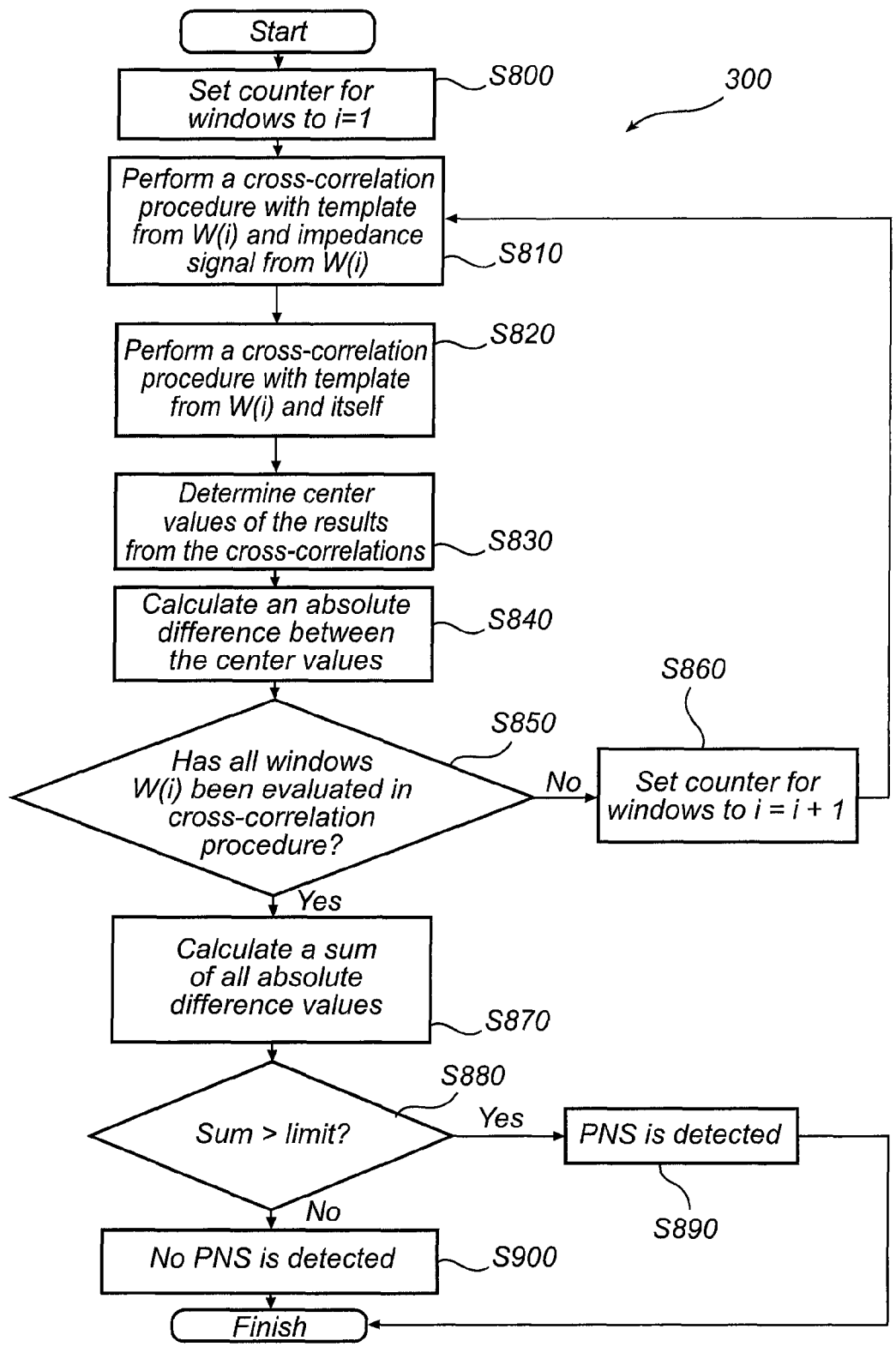
FIG. 13 is a flow chart illustrating steps in a method for PNS detection using cross-correlation between template and impedance signals.

According to embodiments of the present invention, PNS detection using frequency spectrum can also be made. The lungs are expected to change quickly in size at a PNS event. This creates higher frequency components in the impedance signal spectrum. Spectral components will appear in the spectrum at a higher frequency range. The detection of PNS can be made by calculating the area under the obtained frequency spectrum. This area can be compared to an area calculated using a frequency spectrum obtained with and/or without PNS With reference now to FIG. 13, an exemplary embodiment of the present invention for detecting PNS using cross-correlation will be discussed. FIG. 13 illustrates a flow chart describing tasks or steps performed to detect PNS using cross-correlation. The various tasks described in FIG. 13 performed in connection with the processes may be performed by software, hardware, firmware, or any combination thereof. For illustrative purposes, the following description of the processes refers to elements mentioned above in connection with FIGS. 1 and 2. In practical embodiments, portions of the processes may be performed by different elements of the described cardiac stimulator. It should be appreciated that the processes may include any number of additional or alternative tasks or steps, the tasks shown in FIG. 13 need not be performed in the illustrated order, and the processes may be incorporated into a more comprehensive procedure or process having additional functionality not described in detail herein.

In step S800, a counter for the window W(i) is set to i=1. At step S810, a cross-correlation process is performed with the template from W(i) and the obtained impedance signals from the window W(i). Then, at step S820, a cross-correlation process is performed with the template from W(i) and itself. The results from the cross-correlation procedures are stored in a respective vector M1 and M0, respectively. At step S830, center values for the vectors M1 and M0 are determined:

$$m1c = M1(\text{center})$$

$$m0c = M0(\text{center})$$

Thereafter, at step S840, the absolute difference between m1c and m0c is calculated:

$$\text{Delta}(i) = abs(m1c - m0c)$$

At step S850, it is checked whether all windows have been evaluated in the cross-correlation procedure 300. If not, the procedure 300 proceeds to step S860 where the counter is set to i=i+1. Then, the procedure 300 returns to steps S810-S850. On the other hand, if all windows have been evaluated, the procedure 300 proceeds to step S870 where all absolute difference components are summed:

$$\text{Delats\_sum} = \text{sum}(\text{delta})$$

In step S880, the sum is compared to a predetermined test limit. The test criteria will depend on whether a template with or without PNS is used. If a template without PNS is used, a sum exceeding the test limit will indicate presence of PNS and a sum being below the test limit will indicate that no PNS is present and, inversely, if a template with PNS is used, a sum being below the test limit will indicate presence of PNS and a sum exceeding the test limit will indicate that no PNS is present. In the embodiment illustrated in FIG. 13, a template without PNS content is used. Hence, if the sum exceeds the predetermined test limit in the comparison performed in step S880, the procedure 300 proceeds to step S890 where it is determined that PNS has been detected. On the other hand, if the sum is below the predetermined test limit, the procedure 300 proceeds to step S900 where it is determined that no PNS has been detected.

In embodiments of the present invention, the impedance signals/frequency content obtained from different electrode configurations are merged or weighted with a respective PNS factor, which is based on a difference between a template with PNS content and a template without PNS content. The absolute differences between each sample of the templates with and the template without PNS are summed for each time window. The time window sums are then averaged over the applicable time windows. This should be performed for each impedance configuration. Each average sum (Ai, i=index for impedance configuration) will then be multiplied with a PNS factor, being separate for each impedance configuration. The value of each PNS factor is controlled by the following rule:

$$A1 * PNS\text{factor}1 = A2 * PNS\text{factor}2 = \ldots = Ak * PNS\text{factor}k$$

The steps above should be carried out for each body posture and activity. When the impedance signals from each impedance configuration shall be combined as input to the PNS detection analysis, each impedance signal shall be multiplied with the PNS factor belonging to respective impedance configuration. If the PNS detection is carried out using frequency spectra the same procedures as above can be carried out using the frequency components in the selected frequency range instead of the impedance signals. The calculated differences mentioned above are in this case obtained by subtraction of each spectral component of the spectrum with and without PNS.

According to embodiments of the present invention, the PNS test includes measuring impedance signals in time windows synchronized with the delivery of a pacing pulse in the refractory period of the left ventricle using more than one electrode configuration in a time window or alternately using different electrode configurations for different time windows. Furthermore, at least one measured impedance signal is gathered from each time window and for each electrode configuration and the gathered impedance signals values for each electrode configuration are compared with a corresponding impedance signal template for each electrode configuration and a PNS factor is applied for each electrode configuration.

According to embodiments of the present invention, combinations of impedance measurement vectors are used for detecting PNS. At regular intervals and/or at detection of a specific posture and/or a specific activity level and/or at occurrence of a predetermined hemodynamic event the PNS test is performed. The pacing module repeatedly delivers pacing pulses within a refractory period of the left ventricle of the heart during a number of cardiac cycles, which pacing pulses have a predetermined amplitude/width. The impedance measurement module measures impedance signals in time windows synchronized with the delivery of a pacing pulse in the refractory period of the left ventricle using more than one electrode configuration in a time window or alternately using different electrode configurations for different time windows. Further, the PNS detection module gathers at least one measured impedance signal from each time window and for each electrode configuration and analyzes the gathered impedance signals to detect morphological events and/or deviations indicating PNS by comparing the gathered impedance signals for each electrode configuration with a corresponding impedance signal template per time window for each electrode configuration and applying a PNS factor for each electrode configuration.

In embodiments of the present invention, a difference waveform between a measured impedance waveform and each corresponding template for each electrode configuration is calculated and a difference value for each electrode configuration is determined. Each difference value is multiplied with the corresponding PNS factor to determine a resulting value for each electrode configuration, the resulting values for all electrode configurations are added and it is determined that PNS has occurred if the added resulting values are higher than a predetermined PNS threshold.

According to embodiments of the present invention, a PNS factor is calculated for each electrode configuration reflecting a difference between an impedance signal template with PNS content and an impedance signal template without PNS content for that specific electrode configuration. Alternatively, the PNS factor for each electrode configuration reflects a difference between frequency content in an impedance waveform with PNS content and frequency content in an impedance waveform without PNS content.

Although certain embodiments and examples have been described herein, it will be understood by those skilled in the art that many aspects of the devices and methods shown and described in the present disclosure may be differently combined and/or modified to form still further embodiments. Alternative embodiments and/or uses of the devices and methods described above and obvious modifications and equivalents thereof are intended to be within the scope of the present disclosure. Thus, it is intended that the scope of the present invention should not be limited by the particular embodiments described above, but should be determined by a fair reading of the claims that follow.

The invention claimed is:

1. An implantable medical device connectable to a plurality of electrodes electrically coupled to a heart of a patient in at least one electrode configuration, comprising:
 a pacing module configured to deliver pacing pulses to the heart using said at least one electrode configuration;
 a control module configured to instruct said pacing module to deliver pacing pulses having a predetermined pulse amplitude and/or width within the refractory period of the left ventricle, wherein said pacing pulses are repeatedly delivered during a number of cardiac cycles and wherein said pacing pulses are delivered at different predetermined delays relative to an onset of the refractory period of the left ventricle in different cardiac cycles;
 an impedance measurement module configured to measure impedance signals in time windows synchronized with said delivery of pacing pulses in said refractory period of the left ventricle using at least one electrode configuration;
 a phrenic nerve stimulation, PNS, detection module configured to:
 gather at least one impedance signal from each time window;
 create aggregated impedance signals using the impedance signals from the different time windows; and
 analyze the aggregated impedance signals to detect PNS.

2. The implantable medical device according to claim 1, wherein said PNS detection module is configured to analyze the aggregated impedance signals to detect morphological events and/or deviations indicating PNS by comparing said gathered impedance signals with at least one impedance signal template per time window.

3. The implantable medical device according to claim 1, wherein said control module is configured to instruct said pacing module to deliver said pacing pulses at said different delays relative to the onset of the refractory period of the left ventricle in different cardiac cycles, wherein the onset of the refractory period of the left ventricle is determined to be a delivery of a stimulation pulse resulting in a left ventricle contraction or a spontaneous ventricle contraction.

4. The implantable medical device according to claim 1, wherein said control module is configured to instruct said pacing module to deliver said pacing pulses via at least a first electrode configuration and wherein said impedance measurement module is configured to measure at least one impedance signal using at least a second electrode configuration.

5. The implantable medical device according to claim 1, wherein said control module is configured to, at predetermined time intervals or at receipt of an instruction, perform a template creation procedure.

6. The implantable medical device according to claim 1, wherein said control module is configured to monitor changes in lead system criteria and, at detection of a change in at least one lead system criteria exceeding a predetermined threshold, to perform a template creation procedure and/or instruct said pacing module to change electrode configuration for delivery of pacing pulses and/or to issue an alert.

7. The implantable medical device according to claim 1, further comprising a posture sensor configured to sense a posture of the patient and/or an activity sensor configured to sense an activity level of the patient.

8. The implantable medical device according to claim 1, wherein said control module is configured to perform a template creation procedure comprising:
 instructing said impedance measurement module to measure impedance signals in time windows in said refractory period of the left ventricle at predetermined delays relative to the onset of said refractory period of the left ventricle using at least one electrode configuration; and
 instructing said PNS detection module to create two or more impedance signal template using said gathered impedance signals.

9. The implantable medical device according to claim 1, comprising a posture sensor configured to sense a posture of the patient and wherein said control module is configured to perform a template creation procedure comprising:
 instructing said pacing module to deliver at least one pacing pulse having a predetermined pulse amplitude and/or width in at least one time window within a refractory period of the left ventricle during a number of cardiac cycles for at least one posture, wherein pacing pulses are repeatedly delivered during a number of cardiac cycles;
 instructing said impedance measurement module to measure impedance signals in time windows synchronized with said delivery of pacing pulses in said refractory period of the left ventricle using at least one electrode configuration; and instructing said PNS detection module to:

gather impedance signals measured within said time windows of said cardiac cycles for said different postures; and create two or more impedance signal templates for said at least one posture using said gathered impedance signals.

10. The implantable medical device according to claim 1, further comprising an activity sensor configured to sense an activity level of the patient and wherein said control module is configured to perform a template creation procedure comprising:

instructing said pacing module to deliver at least one pacing pulse having a predetermined pulse amplitude and/or width in at least one time window within a refractory period of the left ventricle during a number of cardiac cycles at different activity levels, wherein pacing pulses are repeatedly delivered during a number of cardiac cycles;

instructing said impedance measurement module to measure impedance signals in time windows synchronized with said delivery of pacing pulses in said refractory period of the left ventricle using at least one electrode configuration; and instructing said PNS detection module to:

gather impedance signals measured within said time windows of said cardiac cycles for said different activity levels; and create two or more impedance signal templates for each activity level using said gathered impedance signals.

11. The implantable medical device according to claim 1, wherein said control module is configured to perform a template creation procedure comprising:

instructing said pacing module to deliver at least one pacing pulse having a predetermined pulse amplitude and/or width in at least one time window within a refractory period of the left ventricle during a number of cardiac cycles using different electrode configurations, wherein pacing pulses are repeatedly delivered during a number of cardiac cycles;

instructing said impedance measurement module to measure impedance signals in time windows synchronized with said delivery of pacing pulses in said refractory period of the left ventricle using at least one electrode configuration; and instructing said PNS detection module to:

gather impedance signals measured within said time windows of said cardiac cycles; and create at least one impedance signal template for each electrode configuration using said gathered impedance signals.

12. The implantable medical device according claim 8, wherein said PNS detection module is configured to:

receive a verification whether a PNS has occurred or not during the gathering of impedance signals, said verification being received from an extracorporeal unit via a communication module of said implantable medical device; and determine whether a created impedance signal template is a template with PNS content or without PNS content depending on the received verification.

13. The implantable medical device according to claim 8, wherein said PNS detection module is configured to, during a template creation procedure, analyze the gathered impedance signals to determine whether a PNS has occurred or not comprising:

for each time window, calculating the frequency content of the impedance waveform;

determining a frequency content related to respiration;

detecting that a PNS has occurred if said frequency content related to respiration is above a predetermined frequency content threshold for a selected frequency range; and determine whether a created impedance signal template is a template with PNS content or without PNS content depending on whether a PNS was detected or not.

14. The implantable medical device according to claim 1, wherein said control module is configured to, at regular intervals and/or at detection of a specific posture and/or a specific activity level and/or at occurrence of a predetermined hemodynamic event, perform a PNS test comprising:

instructing said pacing module to deliver a pacing pulse having a predetermined pulse amplitude and/or width within a refractory period of the left ventricle, wherein pacing pulses are repeatedly delivered during a number of cardiac cycles;

instructing said impedance measurement module to measure impedance signals in time windows synchronized with said delivery of pacing pulses in said refractory period of the left ventricle using at least one electrode configuration; and instructing said PNS detection module to:

gather at least one measured impedance signal from each time window; and analyze the gathered impedance signals to detect morphological events and/or deviations indicating PNS by comparing said gathered impedance signals with an impedance signal template.

15. The implantable medical device according to claim 1, wherein said control module is configured to:

instruct said PNS detection module to:

gather at least one measured impedance signal from each time window; and analyze the gathered impedance signals to identify a first pulse amplitude and/or width above the pacing therapy threshold that do not cause PNS; and wherein said control module is configured to determine an adequate PNS threshold gap to be the difference between the identified pulse amplitude and/or width and the pacing therapy threshold.

16. The implantable medical device according to claim 1, wherein said control module is configured to initiate a PNS threshold test comprising:

instructing said pacing module to deliver a pacing pulse within a refractory period of the left ventricle of said heart, wherein pacing pulses are repeatedly delivered during a number of cardiac cycles and wherein said pacing pulses having a successively changed pulse amplitude and/or width;

instructing said impedance measurement module to measure impedance signals in time windows synchronized with said delivery of pacing pulses in said refractory period of the left ventricle using at least one electrode configuration; and instructing said PNS detection module to:

gather at least one measured impedance signal from each time window; and analyze the gathered impedance signals to detect morphological events and/or deviations indicating PNS by comparing said gathered impedance signals with impedance signal templates to identify pulse amplitudes and/or widths that do not cause PNS;

wherein said control module is configured to determine the maximum pulse amplitudes and/or widths that do not cause PNS to be a PNS threshold.

17. The implantable medical device according to claim 15, wherein
said control module is configured to determine a PNS threshold gap between a PNS threshold and a pacing therapy threshold, wherein said control module is configured to, at a PNS threshold gap being below a predetermined value, perform an adaptation of pacing settings.

18. The implantable medical device according to claim 15, wherein said control module is configured to, at detection of PNS at a pulse amplitude and/or width below a predetermined threshold for a specific electrode configuration instruct said pacing module to change electrode configuration for delivery of pacing pulses and/or adapt pulse amplitude and/or width.

19. The implantable medical device according to claim 6, wherein said control module is configured to search for another electrode configuration comprising:
selecting an electrode configuration according to a predetermined order of a set of configurations for delivery of pacing pulses;
instructing said pacing module to deliver a pacing pulse having a predetermined pulse amplitude and/or width within a refractory period of the left ventricle during a number of cardiac cycles, wherein pacing pulses are repeatedly delivered during a number of cardiac cycles, for each of said electrode configurations;
instructing said impedance measurement module to measure impedance signals in time windows synchronized with said delivery of pacing pulses in said refractory period of the left ventricle using at least one electrode configuration; and
instructing said PNS detection module to:
gather impedance signals measured within said time windows of said cardiac cycles; and
analyze the gathered impedance signals to detect morphological events or deviations indicating PNS by comparing said gathered impedance signals with impedance signal templates;
wherein said control module is configured to select the electrode configuration for pacing stimulation that provides a predetermined PNS threshold gap.

20. The implantable medical device according claim 1, wherein said PNS detection module is configured to:
for each time window, subtract each impedance sample from a corresponding impedance sample of a selected impedance signal template to obtain absolute difference values;
process said absolute difference values to create an aggregated value for said time windows;
compare said aggregated value with a predetermined limit based on said template; and
detect that a PNS has occurred if said aggregated value is below said predetermined limit.

21. The implantable medical device according to claim 1, wherein said PNS detection module is configured to:
for each time window, subtract each impedance sample from a corresponding impedance sample of a selected impedance signal template to obtain absolute difference values;
process said absolute difference values to create an aggregated value for said time windows;
compare said aggregated value with a predetermined limit based on said template; and
detect that a PNS has occurred if said aggregated value is above said predetermined limit.

22. The implantable medical device according to claim 1, wherein said PNS detection module is configured to:
for each time window, cross-correlate an impedance signal during a time window with an impedance signal template for the corresponding time window to produce a first cross-correlation result;
for each time window, cross-correlate an impedance signal template with itself to produce a second cross-correlation result;
calculate a difference value for each time window between the first and second cross-correlation results;
calculate a sum of all absolute difference values;
compare said sum with a predetermined limit value; and
detect that a PNS has occurred if said aggregated value exceeds said predetermined limit value.

23. The implantable medical device according to claim 1, wherein said PNS detection module is configured to:
for each time window, cross-correlate an impedance signal during a time window with an impedance signal template for the corresponding time window to produce a first cross-correlation result;
for each time window, cross-correlate an impedance signal template with itself to produce a second cross-correlation result;
calculate a difference value for each time window between the first and second cross-correlation results;
calculate a sum of all absolute difference values;
compare said sum with a predetermined limit value; and
detect that a PNS has occurred if said aggregated value is below said predetermined limit value.

24. The implantable medical device according to claim 1, wherein said PNS detection module is configured to:
for each time window, determine a number of points in the impedance waveform where a derivative of the impedance waveform shows a change of sign, wherein a new sign of the derivative lasts a predetermined period of time; and
detect that a PNS has occurred if a difference between a determined number of points and a reference number of points is higher than or equal to a predetermined limit value.

25. The implantable medical device according to claim 1, wherein said PNS detection module is configured to:
for each time window, calculate the frequency content of the impedance waveform;
compare the calculated frequency content with a frequency content of a selected impedance template; and
detect that a PNS has occurred if a deviation between the calculated frequency content and the frequency content of the selected impedance template is above a predetermined frequency content threshold for a selected frequency range.

26. The implantable medical device according to claim 1, wherein said control module is configured to, at regular intervals and/or at detection of a specific posture and/or a specific activity level and/or at occurrence of a predetermined hemodynamic event, initiate a PNS test comprising:
instructing said pacing module to repeatedly deliver pacing pulses within a refractory period of the left ventricle of said heart during a number of cardiac cycles, said pacing pulses having a predetermined pulse amplitude and/or width; and instructing said impedance measurement module to measure impedance signals in time windows synchronized with said delivery of a pacing pulse in said refractory period of the left ventricle using more than one electrode configuration in a time window or alternately using different electrode configurations for different time windows;

instructing said PNS detection module to:

gather at least one measured impedance signal from each time window and for each electrode configuration; and analyze the gathered impedance signals to detect morphological events and/or deviations indicating PNS by comparing said gathered impedance signals for each electrode configuration with a corresponding impedance signal template for each electrode configuration and applying an PNS factor for each electrode configuration.

27. The implantable medical device according to claim 26, wherein said PNS detection module is, so as to detect morphological events and/or deviations indicating PNS, configured to:

calculate a difference waveform between a measured impedance waveform and each corresponding template for each electrode configuration;

determine a difference value for each electrode configuration;

multiply each difference value with the corresponding PNS factor to determine a resulting value for each electrode configuration;

add the resulting values for all electrode configurations; and detect that PNS has occurred if the added resulting value is higher than a predetermined PNS threshold.

28. The implantable medical device according to claim 26, wherein said PNS detection module is configured to calculate a PNS factor for each electrode configuration as reflecting a difference between an impedance signal template with PNS content and an impedance signal template without PNS content for that specific electrode configuration.

29. The implantable medical device according to claim 26, wherein said control module is configured to instruct said pacing module to deliver pacing pulses having predetermined energies within a refractory period of the left ventricle, wherein pacing pulses are repeatedly delivered during a number of cardiac cycles; wherein said impedance measurement module is configured to measure impedance signals in time windows synchronized with said delivery of pacing pulses in said refractory period of the left ventricle using more than one electrode configuration simultaneously or alternately using different electrode configurations for different time windows; and wherein said PNS detection module is configured to:

gather at least one impedance signal from each time window and for each electrode configuration; and calculate a PNS factor for each electrode configuration reflecting a difference between a frequency content in an impedance waveform with PNS content and a frequency content in an impedance waveform without PNS content.

* * * * *